United States Patent
Arcot-Krishnamurthy et al.

(10) Patent No.: US 9,314,627 B2
(45) Date of Patent: Apr. 19, 2016

(54) SYSTEMS AND METHODS TO ACCOUNT FOR NECK MOVEMENT DURING NERVE STIMULATION

(75) Inventors: Shantha Arcot-Krishnamurthy, Vadnais Heights, MN (US); Stephen Ruble, Lino Lakes, MN (US); Jason J. Hamann, Blaine, MN (US); Juan Gabriel Hincapie Ordonez, Maple Grove, MN (US); David J. Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 939 days.

(21) Appl. No.: 13/453,279

(22) Filed: Apr. 23, 2012

(65) Prior Publication Data

US 2012/0271382 A1   Oct. 25, 2012

Related U.S. Application Data

(60) Provisional application No. 61/478,688, filed on Apr. 25, 2011.

(51) Int. Cl.
*A61N 1/36* (2006.01)

(52) U.S. Cl.
CPC ........ *A61N 1/36053* (2013.01); *A61N 1/36132* (2013.01); *A61N 1/36135* (2013.01); *A61N 1/3611* (2013.01)

(58) Field of Classification Search
CPC .................................................. A61N 1/36185
See application file for complete search history.

(56) References Cited

U.S. PATENT DOCUMENTS

| 5,938,690 A | 8/1999 | Law et al. |
| 2010/0125304 A1 | 5/2010 | Faltys |

FOREIGN PATENT DOCUMENTS

| JP | 2014516297 A | 7/2014 |
| WO | WO-2007112061 A2 | 10/2007 |
| WO | WO-2012148845 A1 | 11/2012 |

OTHER PUBLICATIONS

"International Application Serial No. PCT/US2012/034645, International Preliminary Report on Patentability mailed Nov. 7, 2013", 8 pgs.
"International Application Serial No. PCT/US2012/034645, International Search Report mailed Jul. 11, 2012", 4 pgs.
"International Application Serial No. PCT/US2012/034645, Written Opinion mailed Jul. 11, 2012", 6 pgs.
"Japanese Application Serial No. 2014-508462, Office Action mailed Oct. 1, 2014, with English translation", 4 pgs.

*Primary Examiner* — Paula J Stice
(74) *Attorney, Agent, or Firm* — Schwegman Lundberg & Woessner, P.A.

(57) ABSTRACT

Some embodiments provide a method, comprising performing a neural stimulation test routine for stimulating a neural target in a cervical region of a patient, wherein for each of a plurality of head positions, performing the neural stimulation test routine includes testing a plurality of electrode configurations. The method further comprises recording threshold data for each of the tested electrode configurations for the plurality of head positions, and recommending an electrode configuration based on the recorded threshold data.

25 Claims, 15 Drawing Sheets

| | CATHODE (NEG. TERM.) → NODE | HEAD STRAIGHT | HEAD RIGHT | HEAD LEFT | MAX. THRESHOLD |
|---|---|---|---|---|---|
| ELECTRODE CONFIG. 1 | 1 → 2 | 2.5 | 3 | 2.5 | 3 |
| ELECTRODE CONFIG. 2 | 2 → 1 | 2 | 2 | 2 | 2 |
| ELECTRODE CONFIG. 3 | 3 → 4 | 2 | 1.5 | 1.5 | 2 |
| ELECTRODE CONFIG. 4 | 4 → 3 | 1.7 | 1.5 | 1.5 | 1.7 |

| CATHOD → ANODE | TURNED RIGHT SIDE | HEAD RIGHT 45 | HEAD STRAIGHT | HEAD LEFT 45 | TURNED LEFT SIDE | MAX LARYNGEAL (MIN PHRENIC) |
|---|---|---|---|---|---|---|
| 1 → 2 | 1.5 (3) | 0.8 (3) | 0.7 (10) | 0.7 (NC) | 0.4 (0.8) | 1.5 (0.8) |
| 2 → 1 | 1.5 (3) | 0.9 (10) | 0.9 (NC) | 1.5 (NC) | 0.5 (3) | 1.5 (3) |
| 3 → 4 | 1.5 (NC) | 0.6 (NC) | 0.7 (NC) | 1.5 (NC) | 0.4 (NC) | 1.5 (NC) |
| 4 → 3 | 1.5 (NC) | 0.6 (NC) | 0.6 (NC) | 2 (NC) | 0.8 (NC) | 2 (NC) |

SYSTEMS AND METHODS TO ACCOUNT FOR NECK MOVEMENT DURING NERVE STIMULATION

CLAIM OF PRIORITY

This application claims the benefit of priority under 35 U.S.C. §119(e) of Arcot-Krishnamurthy et al., U.S. Provisional Patent Application Ser. No. 61/478,688, entitled "SYSTEMS AND METHODS TO ACCOUNT FOR NECK MOVEMENT DURING NERVE STIMULATION", filed on Apr. 25, 2011, which is herein incorporated by reference in its entirety.

TECHNICAL FIELD

This application relates generally to medical devices and, more particularly, to systems, devices and methods for delivering neural stimulation.

BACKGROUND

Neural stimulation, such as vagus nerve stimulation, has been proposed as a therapy for a number of conditions. Examples of neural stimulation therapies include neural stimulation therapies for respiratory problems such as sleep disordered breathing, blood pressure control such as to treat hypertension, cardiac rhythm management, myocardial infarction and ischemia, heart failure (HF), epilepsy, depression, pain, migraines, eating disorders and obesity, and movement disorders.

SUMMARY

Some embodiments provide a method, comprising performing a neural stimulation test routine for stimulating a neural target in a cervical region of a patient, wherein for each of a plurality of head positions, performing the neural stimulation test routine includes testing a plurality of electrode configurations. The method further comprises recording threshold data for each of the tested electrode configurations for the plurality of head positions, and recommending an electrode configuration based on the recorded threshold data.

Some embodiments provide a system configured to deliver vagal stimulation therapy (VST) to a vagus nerve of a patient. Some system embodiments comprise a plurality of electrodes configured to be implanted in a cervical region of the patient, and a neural stimulator configured to deliver the VST using at least one electrode configuration from a plurality of potential electrode configurations for the plurality of electrodes. Feedback circuitry is configured to receive an indicator of a physiological response to VST. The feedback circuitry includes at least one of a sensor configured to sense at least one physiological parameter or a user input device configured to receive patient-entered or clinician-entered feedback. A controller is connected to the neural stimulator and to the feedback circuitry. The controller is configured to perform a neural stimulation test routine for stimulating a neural target in a cervical region of a patient, wherein for each of a plurality of head positions, performing the neural stimulation test routine includes testing a plurality of electrode configurations, record threshold data for each of the tested electrode configurations for the plurality of head positions, and recommend an electrode configuration based on the recorded threshold data.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
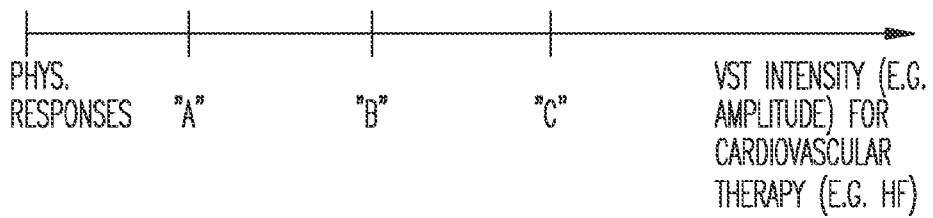
FIG. 1 illustrates intensity thresholds that elicit various physiological responses to VST.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the scope of legal equivalents to which such claims are entitled.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscles around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy, The ANS maintains normal internal function and works with the somatic nervous system. Afferent nerves convey impulses toward a nerve center, and efferent nerves convey impulses away from a nerve center.

Stimulating the sympathetic and parasympathetic nervous systems can cause heart rate, blood pressure and other physiological responses. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intestine, increases urine secretion, and contracts the wall and relaxes the sphincter of the bladder. The functions associated with the sympathetic and parasympathetic nervous systems are many and can be complexly integrated with each other.

A reduction in parasympathetic nerve activity contributes to the development and progression of a variety of cardiovascular diseases. Some embodiments of the present subject matter can be used to prophylactically or therapeutically treat various cardiovascular diseases by modulating autonomic tone. Neural stimulation to treat cardiovascular diseases is referred to herein as neurocardiac therapy (NCT). Vagal stimulation used to treat cardiovascular diseases may be termed either VST or NCT. However, VST may be delivered for non-cardiovascular diseases, and NCT may be delivered by stimulating a nerve other than the vagal nerve. Examples of cardiovascular diseases or conditions include hypertension, HF, and cardiac remodeling. These conditions are briefly described below.

Hypertension is a cause of heart disease and other related cardiac co-morbidities. Hypertension occurs when blood vessels constrict. As a result, the heart works harder to maintain flow at a higher blood pressure, which can contribute to HF. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

HF refers to a clinical syndrome in which cardiac function causes a below normal cardiac output that can fall below a level adequate to meet the metabolic demand of peripheral tissues. HF may present itself as congestive heart failure (CHF) due to the accompanying venous and pulmonary congestion. HF can be due to a variety of etiologies such as ischemic heart disease. HF patients have impaired autonomic balance, which is associated with LV dysfunction and increased mortality.

Cardiac remodeling refers to a complex remodeling process of the ventricles that involves structural, biochemical, neurohormonal, and electrophysiologic factors, which can result following a myocardial infarction (MI) other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

The vagus nerve is a complex physiological structure with many neural pathways that are recruited at different stimulation thresholds. Various physiological responses to vagal stimulation are associated with various thresholds of VST intensity. For example, FIG. 1 illustrates increasing VST intensity from the left side to the right side of the figure, and further illustrates intensity thresholds that elicit various physiological responses to VST. VST causes a physiological response "A" at a lower intensity than an intensity at which VST causes a physiological response "B", which occurs at a lower VST intensity than an intensity at which VST causes a physiological response "C". Stated another way, VST triggers response "A" after reaching a certain level, triggers response "B" along with response "A" after reaching a higher intensity, and triggers response "C" along with responses "A" and "B" after reaching an even higher intensity.

The beneficial effects of VST on cardiac function and remodeling are not necessarily mediated via heart rate reduction. That is, VST can benefit patients without undesired chronotropic effects associated with VST as well as other side effects due to high intensity stimulation such as coughing, muscle stimulation, etc, Rather, anti-inflammatory, anti-sympathetic, and anti-apoptosis mediators are triggered at lower VST intensities than intensities at which a heart rate reduction is realized. These mediators function as pathways through which the VST provides the therapeutic effects for cardiovascular disease.

Physiological responses at the lower VST intensities have therapeutically-effective results for cardiovascular diseases such as HF. These responses mediate or provide pathways for these therapies. Examples of such responses that are beneficial for HF at the lower VST intensities include anti-inflammation, anti-sympathetic, and anti-apoptosis responses, and an increased nitric oxide (NO). Physiological responses at the higher VST intensities may not be desirable. Examples of responses to higher VST intensities that may reduce the ability of the patient to tolerate VST include, but are not limited to, reduced heart rate, prolonged AV conduction, vasodilation, and coughing. At least some of these responses may be desirable for some therapies but not desirable for other therapies. By way of example and not limitation, VST that reduces heart rate and or that prolongs AV conduction may be desirable to treat some cardiovascular diseases, but may not be desirable for other cardiovascular diseases. The intensity of the VST can be adjusted by adjusting parameter(s) of the stimulation signal. For example, the amplitude of the signal (e.g. current or voltage) can be increased to increase the intensity of the signal. Other stimulation parameter(s) can be adjusted as an alternative to or in addition to amplitude. For example, stimulation intensity can vary with the frequency of the stimulation signal (e.g. a frequency of stimulation pulses), a stimulation burst frequency (e.g. a plurality of bursts delivered at a burst frequency for initiating bursts where each burst includes a plurality of pulses), a pulse width and/or a duty cycle.

Figure 2:
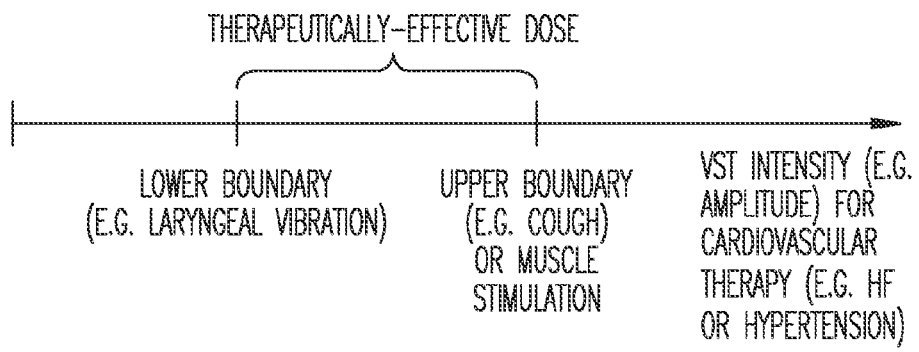
FIG. 2 illustrates an intensity threshold that elicits an undesired physiological response to VST that is used to define an upper boundary for the VST intensity and another intensity threshold that elicits another physiological response to VST, according to various embodiments.

FIG. 2 illustrates increasing VST intensity from the left side to the right side of the figure, and further illustrates an intensity threshold that elicits an undesired physiological response to VST that is used to define an upper boundary for the VST intensity and another intensity threshold that elicits another physiological response to VST. For example, the VST intensity threshold for a cough can be used as an upper boundary, and the VST intensity threshold for a laryngeal vibration response can be used as a lower boundary. In some embodiments, the physiological response to define the upper boundary is detected muscle stimulation. Large muscle stimulation or extraneous stimulation may be bothersome to the patient.

A vagus nerve capture threshold can be set by first recruiting A fibers that cause laryngeal vibrations, and then increasing the intensity until a cough side effect is detected. The intensity is set between the intensity that caused the laryngeal vibrations and the intensity that caused the cough. For example, if the amplitude of the stimulation signal is increased to increase the VST intensity and if 1.0 mA caused laryngeal vibrations and 2.5 mA caused a cough, then the pacing amplitude may be set to 1.0 to 2.4 mA.

Figure 3:
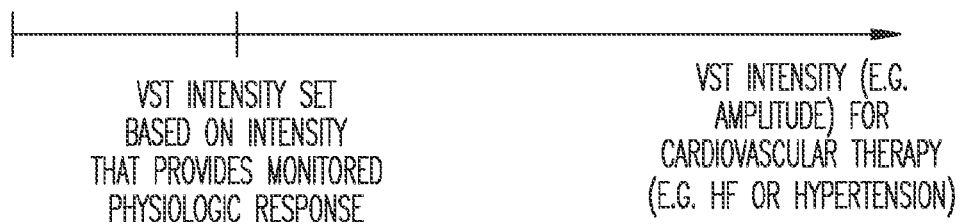
FIG. 3 illustrates that a VST intensity level can be set using the intensity threshold that elicits a physiological response to the VST, according to various embodiments.
Figure 4:
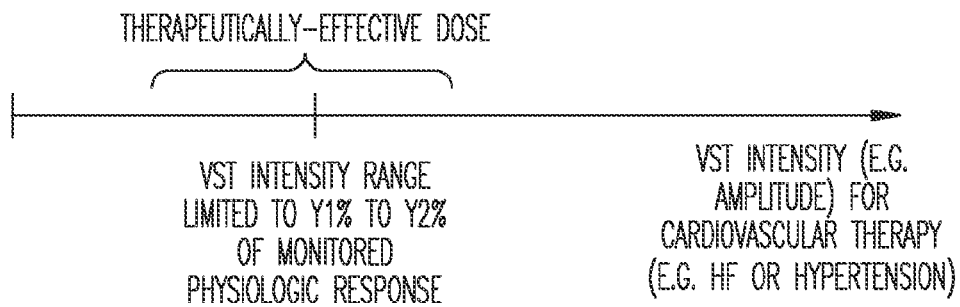
FIG. 4 illustrates using the intensity threshold that elicits a physiological response to set upper and lower limits for a range of VST intensities, according to various embodiments.

FIG. 3 illustrates increasing VST intensity from the left side to the right side of the figure, and further illustrates that a VST intensity level can be set using the intensity threshold that elicits one of the physiological responses to the VST. A monitored physiological response may represent a low stimulation threshold response to VST or higher stimulation threshold responses to VST. For example, if a monitored response is observed at VST intensity level "X", the therapeutically-effective intensity level for the VST can be set as a percentage of "X" (e.g. approximately 75% of "X" or approximately 100% of "X" or approximately 125% of "X") or as an offset "Z" from "X" (e.g. "X" less "Z" or "X" plus "Z"). As generally illustrated in FIG. 4, the intensity threshold that elicits a monitored physiological response can be used to set upper and tower limits for a range of VST intensities. An ability of the device to adjust the VST intensity range may be limited based on the monitored physiological response to the VST. For example, a device may limit adjustments to the VST intensity to Y1% to Y2% of "X" (e.g. 50% to 150%, or 50% to 100%, or 100% to 150% of the stimulation intensity associated with the monitored response). Some embodiments monitor for a low stimulation threshold physiological response to VST such as laryngeal vibration and electroneurographic responses, for example. The stimulation amplitude for VST will be set at or above the current needed to produce the low stimulation threshold physiological response. By way of example, the lower range may be below and the upper range above 100% of "X", the lower and upper ranges may both be below 100% of "X", or may both be above 100% of "X". Alternatively, offsets ("Z1" and/or "Z2" from "X" (not shown)) may be used for at least one of the beginning of the allowable range of intensities or the end of the allowable range of intensities.

Figure 5:
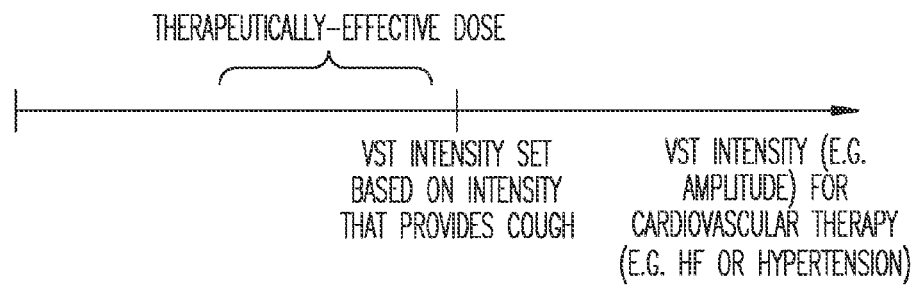
FIG. 5 illustrates the intensity threshold that elicits a physiological response to the VST that is used to set the VST intensity, according to various embodiments.
Figure 6:
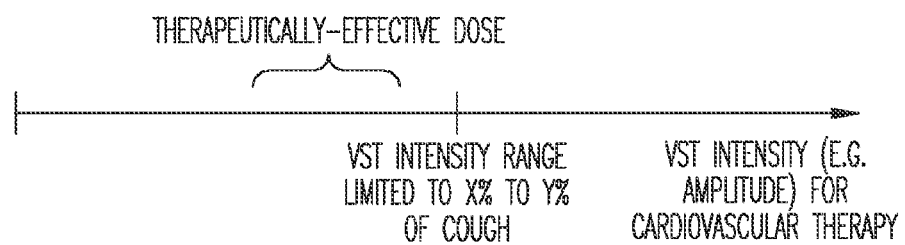
FIG. 6 illustrates using a detected cough response to VST to limit adjustments to the VST intensity range, according to various embodiments.

FIG. 5 illustrates increasing VST intensity from the left side to the right side of the figure, and further illustrates the intensity threshold that elicits a physiological response to the VST that is used to set the VST intensity. For example, if cough is observed, the therapeutically-effective intensity level for the VST can be set as a percentage, and offset, or other function of the VST intensity that elicited the cough. As generally illustrated in FIG. 6, an ability of the device to adjust the VST intensity range may be limited based on the detected cough response to VST. For example, a device may limit adjustments to the VST intensity to a range of percentages or other function of the VST intensity that caused the cough ("X"). By way of example, the tower range may be below and the upper range above 100% of "X", the lower and upper boundaries for the range may both be below 100% of "X", or may both be above 100% of "X". It is currently believed that, for most therapies, both the tower and upper boundaries will be below 100% of the VST intensity "X" that causes cough.

Titration, as used herein, refers to the process of adjusting the dose of the stimulation, ultimately to a level that is therapeutically or prophylactically effective. The titration procedure may occur during an implantation procedure, or during a follow-up clinical visit, or while a patient is ambulatory away from the clinical setting. The titration may be physician-controlled or automatically-controlled based on device programming. The dose includes an amount or intensity of the neural stimulation at a given time frame, and also includes the number of times the neural stimulation is delivered over a period of time. The intensity of the neural stimulation may be adjusted by adjusting parameters such as amplitude, duty cycle, duration, and or frequency of the neural stimulation, or the number of neural stimulation events that occur over a period of time.

Figure 7:
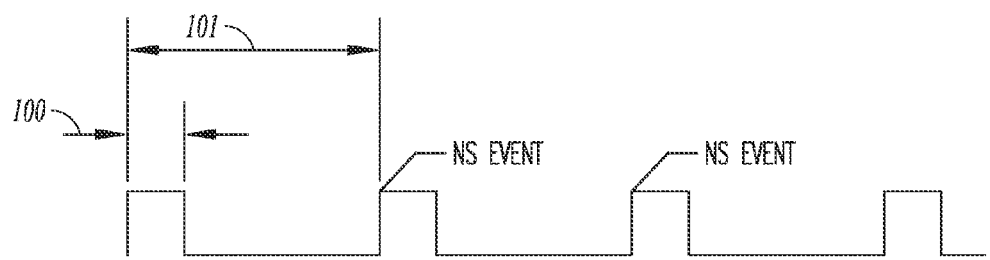
FIG. 7 illustrates a representation of intermittent neural stimulation (INS), according to various embodiments.

FIG. 7 illustrates a representation of intermittent neural stimulation (INS). The figure diagrammatically shows the time-course of a neural stimulation that alternates between intervals of stimulation being ON, when one stimulation pulse or a set of grouped stimulation pulses (i.e., a burst 100) is delivered, and intervals of stimulation being OFF, when no stimulation pulses are delivered. Thus, for example, some embodiments deliver a plurality of monophasic or biphasic pulses within a neural stimulation burst illustrated in FIG. 7. Pulses delivered within a burst 100 may be delivered at a pulse frequency. These pulses also have an amplitude. Both the pulse frequency and the pulse amplitude affect the dose of the neural stimulation therapy. The duration of the stimulation ON interval is sometimes referred to as the stimulation duration or burst duration. The burst duration also affects the dose of the neural stimulation therapy. The start of a stimulation ON interval is a temporal reference point NS Event. The time interval between successive NS Events is the INS Interval, which is sometimes referred to as the stimulation period or burst period 101. The burst period 101 or the number of neural stimulation events that occur over a time period also affect the dose of the neural stimulation. For an application of neural stimulation to be intermittent, the stimulation duration (i.e., ON interval) is less than the stimulation period (i.e., Interval) when the neural stimulation is being applied. The duration of the OFF intervals of INS are determined by the durations of the ON interval and the NS Interval. The duration of the ON interval relative to the INS Interval (e.g., expressed as a ratio) is sometimes referred to as the duty cycle of the INS.

Figure 9:
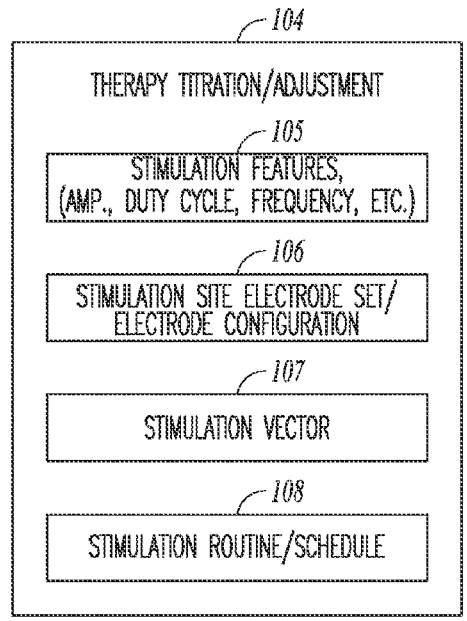
FIG. 9 illustrates an embodiment of a therapy titration module.

A physician or clinician may control the adjustment of one or more neural stimulation parameters to control the stimulation intensity. For example, during an implantation procedure in which stimulation electrodes are implanted near a vagus nerve or other neural stimulation target, the physician or clinician may adjust stimulation parameter(s) to adjust the stimulation intensity to appropriately position the electrodes and program the stimulation to provide threshold stimulation of the neural target that provides a desired physiological effect. The physician or clinician may re-program an implantable neural stimulator during a follow-up visit, to account for migration of the electrodes, changes in impedance in the electrode/tissue interface, and the like. During the follow-up visit, the physician or clinician may control the adjustment of one or more neural stimulation parameters to control the stimulation intensity to determine a neural stimulation intensity that provides the desired physiological response. The titration routine can be an automatic process for an implantable neural stimulation device implanted in an ambulatory patient, such as generally illustrated in FIG. 9. The automatic titration routine can be manually triggered by a signal from a patient or by the physician or clinician. The automatic titration routine can be automatically triggered by a programming schedule or by a sensed event.

Figure 8:
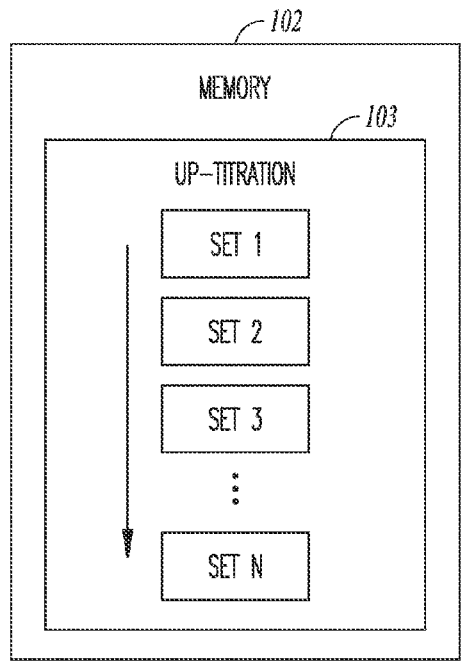
FIG. 8 illustrates a memory, according to various embodiments, that includes instructions, operable on by the stimulation control circuitry, for controlling an up-titration routine by progressively stepping up through defined parameter sets, where each set incrementally changes the stimulation dose or intensity of the stimulation therapy.

FIG. 8 illustrates a memory 102, according to various embodiments, that includes instructions 103, operable on by the stimulation control circuitry, for controlling an up-titration routine by progressively stepping up through defined parameter sets (e.g. parameter set 1 through parameter set N), where each set incrementally changes (increases or decreases) the stimulation dose or intensity of the stimulation therapy. This memory may be illustrated as part of a therapy titration/adjustment module 104 in FIG. 9. The memory may include a plurality of neural stimulation parameter sets, where each set includes a unique combination of parameter values for the neural stimulation and wherein each unique combination of parameter values is defined to provide neural stimulation therapy at an intensity level. The instructions include instructions for stepping through the plurality of neural stimulation parameter sets according to a schedule to change (increase or decrease) the intensity of the therapy until the therapy is at the desired long term intensity. Various embodiments provide a neural stimulation routine that automatically finds the desirable combination of therapy parameters (e.g. amplitude, pulse width, duty cycle) that provides a desired therapy intensity level.

FIG. 9 illustrates an embodiment of a therapy titration module 104, which may also be referred to as a therapy adjustment module. According to various embodiments, the stimulation control circuit is adapted to set or adjust any one or any combination of stimulation features 105. Examples of stimulation features include the amplitude, frequency, polarity and wave morphology of the stimulation signal. Examples of wave morphology include a square wave, triangle wave, sinusoidal wave, and waves with desired harmonic components to mimic naturally-occurring baroreflex stimulation. Some embodiments of the stimulation output circuit are adapted to generate a stimulation signal with a predetermined amplitude, morphology, pulse width and polarity, and are further adapted to respond to a control signal from the controller to modify at least one of the amplitude, wave morphology, pulse width and polarity. Some embodiments of the neural stimulation circuitry are adapted to generate a stimulation signal with a predetermined frequency, and are further adapted to respond to a control signal from the controller to modify the frequency of the stimulation signal.

The therapy titration module 104, also referred to as a therapy adjustment module, can be programmed to change an electrode set or electrode configuration or to change stimulation sites 106, such as changing the stimulation electrodes used for a neural target or changing the neural targets for the neural stimulation. For example, different electrodes can be used to stimulate a neural target, and different electrodes can be used to stimulate different neural targets. A desirably tow stimulation threshold for a neural target may be determined using different electrode sets/configurations for stimulating that neural target. Different neural targets can include different neural pathways such as the right and left vagus nerves and branches thereof, baroreceptors, the carotid sinus, and the carotid sinus nerve. Different neural targets may include different positions along a neural pathway (e.g. more caudal or more cranial targets along a cervical vagus nerve). Autonomic neural targets can include afferent pathways and efferent pathways and can include sympathetic and parasympathetic nerves. The stimulation can include stimulation to stimulate neural traffic or stimulation to inhibit neural traffic. Thus, stimulation to evoke a sympathetic response can involve sympathetic stimulation and/or parasympathetic inhibition; and stimulation to evoke a parasympathetic response can involve parasympathetic stimulation and/or sympathetic inhibition.

The therapy titration module 104 can be programmed to change stimulation vectors 107. Vectors can include stimulation vectors between electrodes, or stimulation vectors for transducers. For example, the stimulation vector between two electrodes can be reversed. More complicated combinations of electrodes can be used to provide more potential stimulation vectors between or among electrodes.

The therapy titration module 104 can be programmed to control the neural stimulation according to stimulation instructions, such as a stimulation routine or schedule 108, stored in memory. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow amore complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time. Duty cycle is specified by the ON time and the cycle time, and thus can have units of ON time/cycle time. According to some embodiments, the control circuit controls the neural stimulation generated by the stimulation circuitry by initiating each pulse of the stimulation signal. In some embodiments, the stimulation control circuit initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the stimulation control circuit controls the stimulation output circuit to initiate a neural stimulation session and to terminate the neural stimulation session. The burst duration of the neural stimulation session under the control of the control circuit can be programmable. The controller may also terminate a neural stimulation session in response to an interrupt signal, such as may be generated by one or more sensed parameters or any other condition where it is determined to be desirable to stop neural stimulation.

A device may include a programmed therapy schedule or routine stored in memory and may further include a clock or timer which can be used to execute the programmable stimulation schedule. For example, a physician can program a daily/weekly schedule of therapy based on the time of day. A stimulation session can begin at a first programmed time, and can end at a second programmed time. Various embodiments initiate and/or terminate a stimulation session based on a signal triggered by a user. Various embodiments use sensed data to enable and/or disable a stimulation session.

According to various embodiments, the stimulation schedule refers to the time intervals or period when the neural stimulation therapy is delivered. A schedule can be defined by a start time and an end time, or a start time and a duration. Various schedules deliver therapy periodically. By way of example and not limitation, a device can be programmed with a therapy schedule to deliver therapy from midnight to 2AM every day, or to deliver therapy for one hour every six hours, or to deliver therapy for two hours per day, or according to a more complicated timetable. Various device embodiments apply the therapy according to the programmed schedule contingent on enabling conditions, such as sensed exercise periods, patient rest or sleep, a particular position/posture, low heart rate levels, and the like. For example, the stimulation can be synchronized to the cardiac cycle based on detected events that enable the stimulation. The therapy schedule can also specify how the stimulation is delivered.

Some embodiments are configured to change a ramp-up time for increasing one or more stimulation parameters from OFF to a programmed intensity at the start of the ON portion. Patients may tolerate higher stimulation levels if there is not an abrupt change at the start of the duty cycle. The parameter increased during this ramp-up time may be amplitude, for example, or other parameter or other combination of parameters that affect the intensity of the stimulation.

Some embodiments of the present subject matter us a multipolar lead to assess vagus capture and side-effects at varied neck positions. Some embodiments use sensors to collect neural stimulation threshold data at varied neck positions, some embodiments use physician and/or patient feedback to collect neural stimulation threshold data at varied neck positions, and some embodiments use both sensors and physician/patient provided feedback to collect neural stimulation threshold data at varied neck positions.

Embodiments of the present subject matter include a programmed algorithm to recommend a pacing electrode configuration using the collected threshold data. For example, an embodiment of the algorithm recommends the most robust configuration for laryngeal capture and the least susceptible configuration for side effects such as cough, phrenic nerve stimulation, large muscle stimulation and the like.

Some embodiments of the present subject matter change the lead/electrode configuration for the stimulation lead based on head position. It has been observed that the electrode configuration that makes the bet nerve capture changes when the head is turned from a straight forward position to either the left or the right.

The collected threshold data for the different head positions may be stored in a lookup table that can be used to document changes in electrode pair(s) and preferences as neck movement changes. The table can be completed by testing the stimulation threshold for the different neck positions. The data contained in the table can be updated with follow-up testing to account for changes caused by lead migration, changes in the electrode/tissue interface, and the like.

Some embodiments provide a default electrode configuration. It is currently believed that better electrode contact with the vagus nerve is made using more caudal electrode configurations (i.e. those electrode configurations that are closer to the thorax). It is believed that the electrodes closer to the thorax are more stable as the head and neck changes positions, and that more cranial (higher) electrodes are moved further away from the stimulation target as the head and neck changes positions.

The changes in the head and neck positions can be measured using strain sensors. For example, the strain sensors can sense changes in strain from the normal straight-facing head positions. Examples of strain sensor technology include piezoelectric, optical, sonar and the like. For example, the sensors can be used to detect if the head turns right or left which can cause twists and torques in the neck, the sensors can be used to detect if the head tilts toward the left or toward the right, and the sensors can be used to detect if the head tilts backward or forward.

Electrodes within a vessel (e.g. internal jugular vein) use to deliver transvenous stimulation or within the carotid sheath used to deliver trans-sheath) stimulation may move away from a targeted vagus nerve with neck movement. The carotid sheath refers to the fibrous connective tissue that surrounds the carotid artery and related structures in the neck. The carotid sheath contains the carotid arteries, the internal jugular vein, and the vagus nerve. The glossopharyngeal nerve and accessory nerve courses in the upper part of the carotid sheath, and the hypoglossal nerve passes through or near the carotid sheath. Thus, head and neck movement can affect the neural stimulation threshold for stimulation of the vagus nerve. Similarly, the stimulation threshold for stimulating the baroreflex near the carotid sinus (e.g. stimulating the carotid sinus nerve or glossopharyngeal nerve or baroreceptor nerve endings) may be affected by head and neck movement if electrodes in a vessel or carotid sheath are used to deliver the stimulation.

Figure 10A:
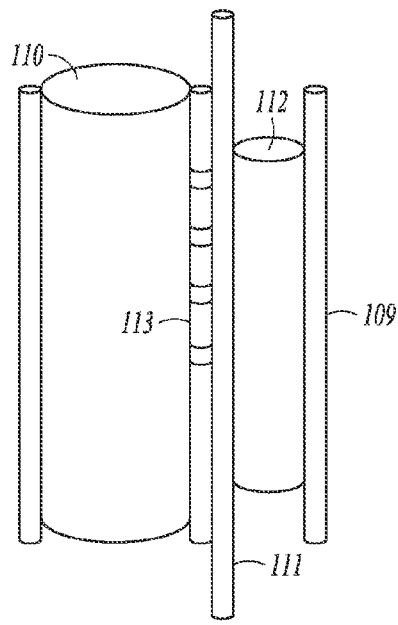
FIGS. 10A and 10B illustrate an embodiment that includes a multipolar lead, along with the carotid sheath, with the internal jugular vein, the vagus nerve and the common carotid artery therein.
Figure 10B:
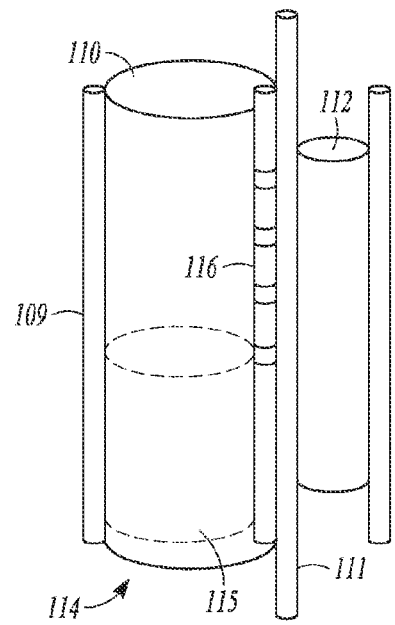

FIGS. 10A and 10B illustrate an embodiment that includes a multipolar lead, along with the carotid sheath 109, with the internal jugular vein 110, the vagus nerve 111 and the common carotid artery 112 therein. Also illustrated in FIG. 10A is a multipolar lead 113 fed proximate to the vagus nerve within the carotid sheath. FIG. 10B illustrates an intravascular structure 114 within the internal jugular vein and proximate to the vagus nerve. The illustrated structure includes an expandable stent 115 connected to a multipolar lead 116, where the expandable stent anchors the multipolar lead in the internal jugular vein. The stent is an example, and may not be needed for fixation.

Various embodiments of the present subject matter use a multipolar lead to assess capture of the neural target and/or side-effects from the neural stimulation at varied head and neck positions. For example, various embodiments of the present subject matter use a multipolar lead to assess capture of a cervical vagus nerve through laryngeal capture and/or vagal stimulation side-effects, such as cough, phrenic nerve capture or muscle capture, at varied head and neck positions. Threshold data is collected for the desired neural stimulation response and/or the side-effect to the neural stimulation. This threshold data may be collected using sensors such as an accelerometer, a pressure sensor, an impedance sensor, a minute ventilation sensor, an electrocardiogram (EKG) for detecting cardiac electrical activity, an electromyogram (EMG) for detecting electrical activity associated with muscle contractions and nerve conduction, and/or blood pressure sensors.

Examples of systems and methods for using an accelerometer to detect threshold data used to control NCT is found in U.S. Pub. No. 2011/0015704 entitled "Physiological Vibration Detection In An Implanted Medical Device," which is herein incorporated by reference in its entirety. Examples of systems and methods for using sensed pressure to detect threshold data used to control NCT is found in U.S. Application 61/427985 entitled "Systems and Methods for Using Sensed Pressure for Neuro Cardiac Therapy," which is herein incorporated by reference in its entirety. Examples of systems and methods for using electrical impedance to detect threshold data used to control NCT is found in U.S. Application 61/427978 entitled "Systems and Methods for Using Electrical Impedance for Neuro Cardiac Therapy," which is herein incorporated by reference in its entirety. Various combinations of the lead electrodes and the can provide various vectors that can be used to calculate impedance between or among these various combinations. Laryngeal vibrations or cough affects the electrode-tissue contact, which affects the sensed parameter (e.g. impedance). The sensor may be internal sensors or external sensors. Additionally or alternatively, the threshold data may be collected using feedback from a patient or a physician. For example a click pad with an assessment scale, such as a pain assessment scale that asks the patient to rate the severity of pain that the patient is experiencing, may be used to record the tolerability or severity of a side effect of the stimulation.

Figures 11, 12:
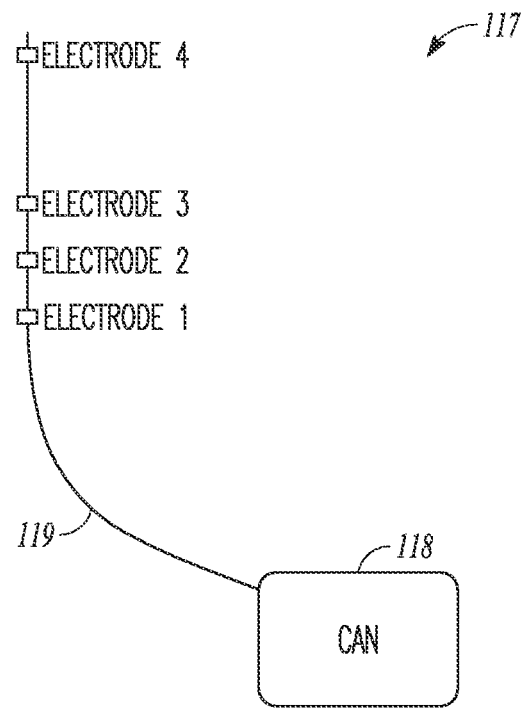
FIG. 11 illustrates an embodiment, by way of example and not limitation, of an implantable medical device with a device housing or can and a lead extending from the can.
FIG. 12 illustrates a table of threshold values, such as may be used in various system embodiments, for various electrode configurations for the device illustrated in FIG. 11.

FIG. 11 illustrates an embodiment, by way of example and not limitation, of an implantable medical device 117 with a device housing or can 118 and a lead 119 extending from the can. The lead includes multiples poles that can be used in various stimulation configurations including unipolar and bipolar configurations. The lead may be an intravascular lead configured to be fed into position through the vasculature of the patient. The lead may be a subcutaneous lead. The lead may be inside or outside the carotid sheath, to provide electrode(s) either adjacent to or surrounding the vagus nerve. The illustrated lead includes four electrodes. However, the present subject matter is not limited to a particular number of electrodes. The can 118 may function as an electrode. In some embodiments, more than one electrode may be on the can 118. The laryngeal vibrations cause the lead and tissue to move with respect to each other, causing the contact between the tissue and the poles to vary. Some poles on the lead can be used to pace, and some embodiments monitor a physiologic response (e.g. impedance) using the poles that are used for pacing. In some embodiments, other poles (other than those used to pace) on the multi-polar lead can be used to monitor a physiologic response. The sensor can be used in combination with other sensors (accelerometer, strain gauge) and/or patient/physician feedback.

FIG. 12 illustrates a table of threshold values, such as may be used in various system embodiments, for various electrode configurations for the device illustrated in FIG. 11. The values in the table indicate that the threshold test was performed using electrodes 1 and 2 as an electrode set, and using electrodes 3 and 4 as an electrode set. The table also indicates the stimulation vector between the electrodes in each electrode set was reversed during the test. For example, in a first electrode configuration identified in row 1, a more negative potential was applied to the first electrode (termed herein as the "negative terminal" or the "cathode") and a more positive potential was applied to the second electrode (termed herein as the "positive terminal" or the "anode"). The terms negative and positive are used as relative terms referring to an electrical potential difference between the electrodes, in which electrons move from the negative terminal/cathode toward the positive terminal/anode. In a second electrode configuration identified in row 2, the second electrode functions as the negative terminal/cathode and the first electrode functions as the positive terminal/anode. In a third electrode configuration identified in row 3, the third electrode functions as the negative terminal/cathode and the fourth electrode functions as the positive terminal/anode. In a fourth electrode configuration identified in row 4, the fourth electrode functions as the negative terminal/cathode and the third electrode functions as the positive terminal/anode. In each of these electrode configurations, the stimulation threshold was determined and recorded when the head was straight, when the head was turned right, and when the head was turned left. The stimulation threshold is recorded as the lowest amplitude of the stimulation current used to stimulate a cervical vagus nerve that caused laryngeal vibration. Laryngeal vibration is used in this example as an indicator that the vagus nerve is being captured by the electrical stimulation. The last column records the maximum threshold recorded for the head positions for each electrode configuration. For example, the recorded thresholds for the first electrode configuration are 2.5 mA when the head is straight, 3 mA, when the head is turned right, and 2.5 mA when the head is turned left; and the maximum recorded threshold for the first electrode configuration is 3 mA (when the head was turned right). The algorithm determines that the lowest maximum threshold is for the fourth electrode configuration, in which the fourth electrode functions as the negative terminal/cathode and the third electrode functions as the positive terminal/anode. Thus, the algorithm recommends using the fourth electrode configuration, in which the most caudal electrode (electrode 4) functions as the negative terminal/cathode. The algorithm determines the desired pacing threshold based on the lowest maximum threshold, which is the maximum threshold for the fourth electrode configuration in this example. For example, and embodiment recommends the pacing threshold to be set at the lowest maximum threshold plus safety factor.

Figures 13, 14:
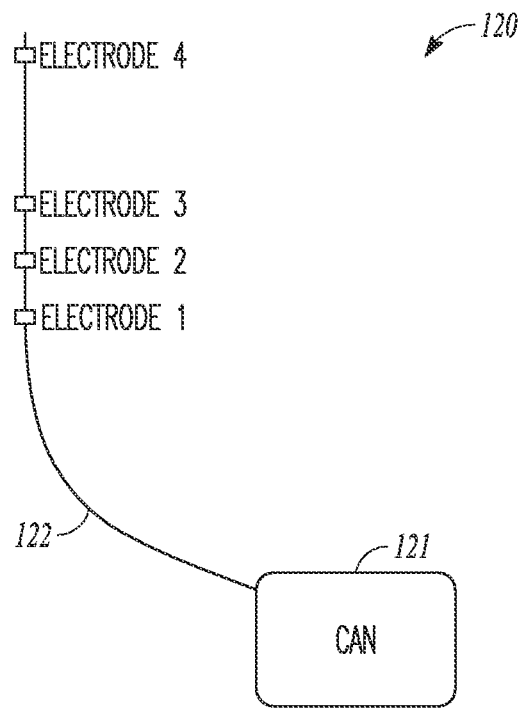
FIGS. 13 and 14 illustrate another example of a device and a table of threshold values, wherein the table records values for both a desired physiological response to the stimulation and an undesired physiological effect or side effect to the stimulation.

FIGS. 13 and 14 illustrate another example of a device and a table of threshold values, wherein the table records values for both a desired physiological response to the stimulation and an undesired physiological effect or side effect to the stimulation. For example, the threshold test for stimulation of the cervical vagus nerve monitors both laryngeal vibration as the desired physiological response and monitors phrenic nerve activity or capture as an undesired physiological response. The implantable medical device 120 of FIG. 13 has a device housing or can 121 and a lead 122 extending from the can. The electrode numbering has been reversed in FIG. 13 in comparison to FIG. 11, such that the first electrode is the most caudal electrode and the fourth electrode is the most cranial electrode.

For each of these electrode configurations, the stimulation threshold is determined and recorded when the head is turned to the right side, when the head is turned to the right about 45 degrees, when the head is straight, when the head is turned to the left about 45 degrees, and when the head is turned to the left side. The stimulation threshold is recorded as the lowest amplitude of the stimulation current used to stimulate a cervical vagus nerve that caused laryngeal vibration. Laryngeal vibration is used in this example as an indicator that the vagus nerve is being captured by the electrical stimulation. In parenthesis, the side effect threshold is recorded as the lowest amplitude of the stimulation current used to stimulate the cervical vagus nerve that still caused the side effect. Phrenic nerve capture is used in this example as an indicator that the vagus nerve stimulation is causing a side effect. The last column records the maximum threshold and the minimum side effect threshold recorded for the head positions for each electrode configuration. In this embodiment for example, the recorded thresholds for the first electrode configuration are 1.5 mA, 0.8 mA, 0.7 mA, 0.7 mA and 0.4 mA, such that the maximum stimulation threshold for the first electrode configuration is 1.5 mA. In this embodiment, the recorded side effect thresholds for the first electrode configuration are 3 mA, 3 mA, 10 mA, no detected phrenic capture or No Capture (NC), and 0.8 mA, such that the minimum side effect threshold for the first electrode configuration is 0.8 mA. Considering all electrode configurations, the lowest maximum stimulation for detecting laryngeal vibration is 1.5 mA, and the largest side effect threshold is no capture (NC). As the third electrode configuration provides both the 1.5 mA maximum stimulation for detecting laryngeal vibration and no phrenic nerve capture, the algorithm recommends the third electrode configuration, with the third electrode as the negative terminal/cathode and the fourth electrode as the positive terminal/anode, and further recommends a pacing threshold based on the 1.5 mA threshold (e,g. 1.5 mA plus a safety factor).

Figure 15:
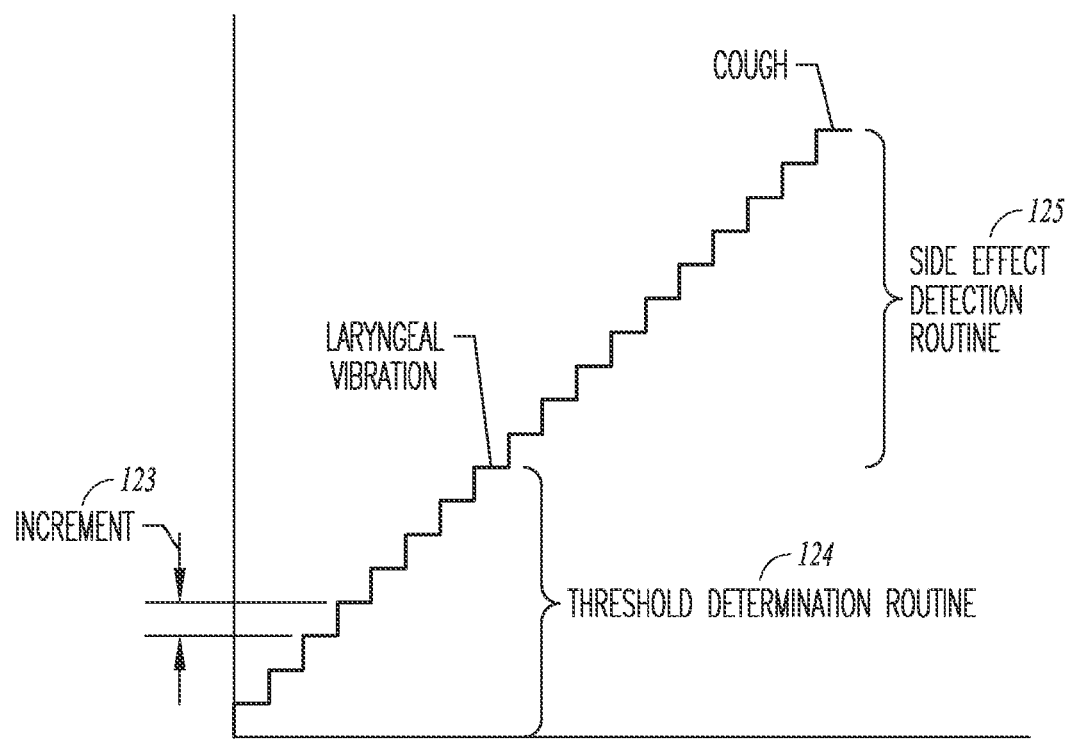
FIG. 15 illustrates an embodiment of a routine for finding threshold values for each of the electrode configurations.

FIG. 15 illustrates an embodiment of a routine for finding threshold values for each of the electrode configurations. The illustrated routine increases the intensity of the neural stimulation therapy over a period of time. The intensity is increased in increments 123. In the illustrated embodiments, a threshold determination routine 124 is performed to detect a lower boundary physiologic response to the neural stimulation such as a laryngeal vibration response. In various embodiments, a side effect detection routine 125 is performed to detect an upper boundary physiologic response (e.g. cough) to the neural stimulation. Some embodiments decrease the intensity of the NCT therapy over a period of time to detect the desired or undesired physiologic responses to the neural stimulation.

Some embodiments use sensors to detect the desired physiological response (e,g, laryngeal vibration) and to detect an undesired response (e,g, cough or phrenic nerve capture). At least some of the sensors may be part of an implantable device, such as an implantable nerve stimulator used to stimulate the target nerve. In some embodiments, at least some of the sensors are part of a programmer/PSA (pacing system analyzer). Examples of sensors include a pressure sensor, an accelerometer, a minute ventilation sensor, an impedance sensor, a sensor configured to detect an electrocardiogram (EKG), a sensor configured to detect an electromyogram (EMG), and a blood pressure sensor. Some embodiments use feedback from a patient or physician. For example, a clicker pad with a pain assessment or other scale can be used to allow the patient to provide feedback as to whether the stimulation provides laryngeal vibration or other desired response and whether the stimulation provides cough or phrenic nerve capture or other undesired physiological response to the stimulation. The algorithm can be implemented in the programmer, or in the implantable device, or in an external device configured to communicate with the programmer and/or the implantable device such as in a patient management system.

Some algorithm embodiments select the electrodes (poles or terminals) for the stimulation using only the side effect thresholds. To save time, some algorithm embodiments limit the current levels that can be tested for the desired stimulation threshold (e.g. laryngeal) and/or for side effect threshold (e.g. cough or phrenic nerve capture or muscle capture). For example the current levels may be limited to 1 mA to determine if the stimulation causes the desired response, and may be limited to 4 mA to determine if the stimulation causes a side effect. Additionally or alternatively, limited head and neck positions may be tested.

Some embodiments use sensors to detect the head and/or neck positions. For example, a strain gauge or a camera can be used to detect the positions. In some embodiments, a clinician or patient determines the head positions and inputs the head positions into a device. In some embodiments, the patient responds to commands to move his or her head into a preprogrammed set of head positions.

In some embodiments, the algorithm determines maximum impedance for the electrode configurations and determines power $P=I^2R$. For example, the algorithm may recommend the electrode configuration that requires the least power for the tested head positions.

In some embodiments, the algorithm prevents the system from being programmed to deliver stimulation above charge injection limits. For example, an electrode surface area, which may be pre-programmed into the algorithm, can be used to estimate charge injection limits.

The algorithm may be expanded to other neural stimulation therapies designed to provide a desired response, such as a desired blood pressure or heart rate response, and/or avoid side effect measures. For example, a neural stimulation therapy that targets the carotid sinus nerve or glossopharyngeal nerve using transvascular or transheath stimulation may implement a similar algorithm to determine the desired stimulation electrodes (e.g. poles or terminals), stimulation vector, and stimulation intensity.

Some embodiments repeat the algorithm periodically or intermittently, such as may be appropriate to account for lead migration and/or therapy optimization. The system (e.g. device or programmer) may be programmed to initiate the algorithm automatically. In some embodiments, the patient initiates the algorithm using an external device or a signal (e.g. magnet or wireless communication) with the implantable device. In some embodiment the physician or clinician initiates the algorithm.

Figure 16:
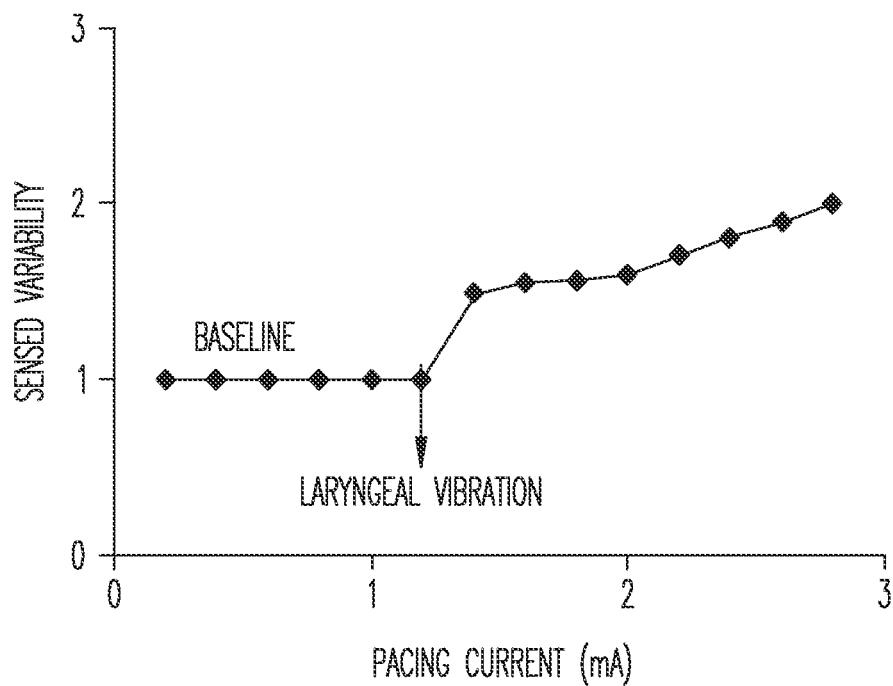
FIG. 16 illustrates a step up in the variability of the sensed physiological parameter, such as impedance, when laryngeal vibrations occur.
Figure 17:
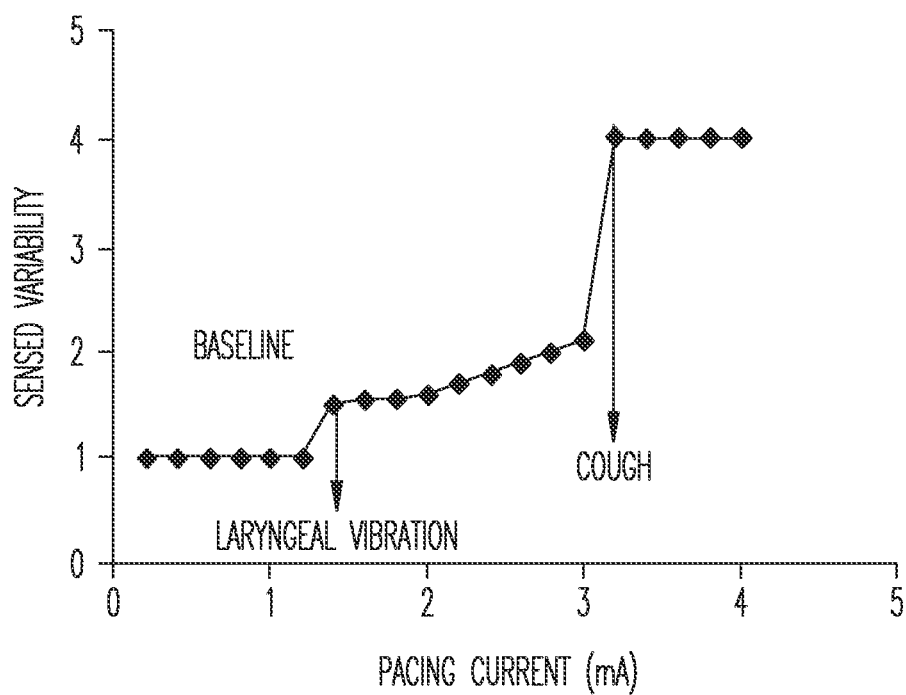
FIG. 17 illustrates a step up in the variability of the sensed physiological parameter when cough occurs.

Various embodiments analyze a plurality of sensed values to detect physiological responses to the NCT, such as laryngeal vibrations and/or cough. Some embodiments correlate the timing of the neural stimulation bursts to the timing of the physiological responses to determine whether the physiological response is attributable to the NCT. FIG. 16 illustrates a step up in the variability of the sensed physiological parameter, such as impedance, when laryngeal vibrations occur. As described elsewhere various embodiments use laryngeal vibration as a desired physiological response to the neural stimulation. FIG. 17 illustrates a step up in the variability of the sensed physiological parameter when cough occurs. As described elsewhere various embodiments use cough as a desired physiological response to the neural stimulation. By way of example and not limitation, some system embodiments monitor a trend of the variability of the sensed parameter as the intensity is increased and detects the physiological response if the trend changes by more than threshold.

Figure 18:
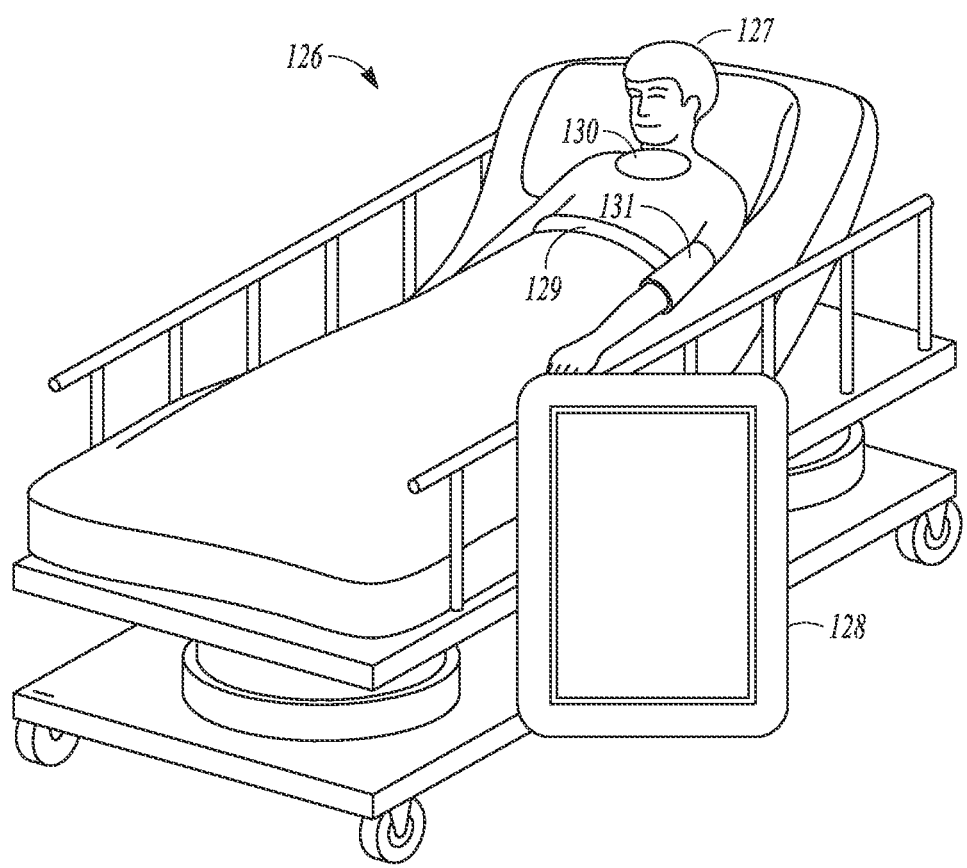
FIG. 18 illustrates an embodiment of a system which could be used to implant neural stimulation electrodes in the cervical region of a patient.

FIG. 18 illustrates an embodiment of a system 126 which could be used to implant neural stimulation electrodes in the cervical region 127 of a patient. For example, the neural stimulation electrodes may be positioned within an internal jugular vein or carotid sheath near a cervical vagus nerve, for use to deliver NCT. A programmer 128 is connected to a respiration sensor 129, an accelerometer 130 positioned to detect laryngeal vibration and/or cough, and a blood pressure sensor/cuff 131. The system performs the algorithm using sensed parameters for different head and neck positions, which is used to program the electrode configuration (including the electrode set and stimulation vectors) and to program the stimulation parameters, such as amplitude, to control the stimulation intensity.

Figure 19:
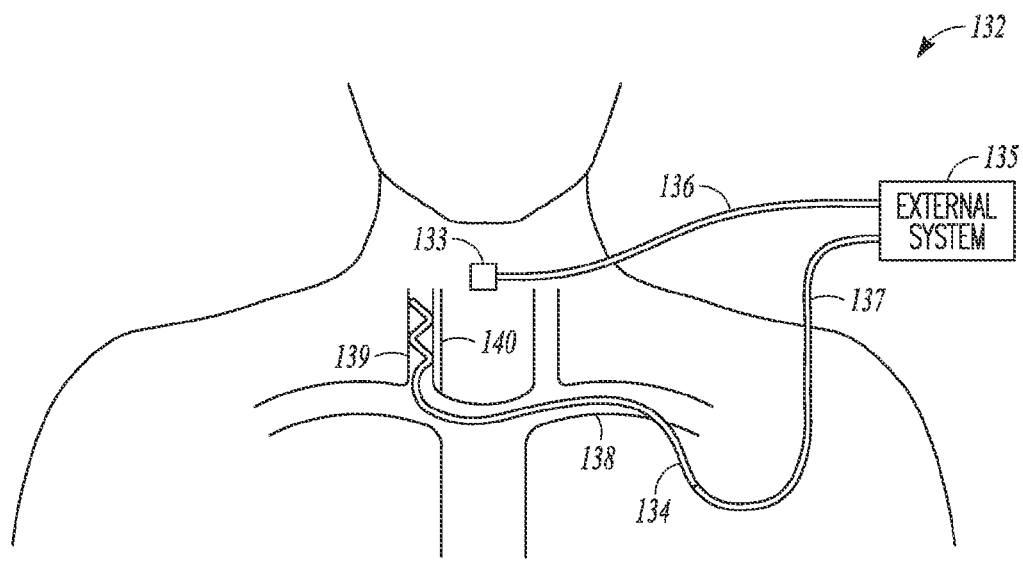
FIGS. 19-20 illustrate embodiments of a neural stimulation system and portions of an environment in which the system is used.

FIG. 19 is an illustration of an embodiment of a neural stimulation system 132 and portions of an environment in which the system is used. The illustrated system includes an activity sensor 133, such as an accelerometer by way of example, for sensing laryngeal activity, a transvenous lead 134 for delivering vagal nerve stimulation, and an external system 135 coupled to the activity sensor via a cable 136 and coupled to lead 134 via a cable 137. The external system 135 includes the algorithm for detecting desired and/or undesired response thresholds to neural stimulation.

A distal end of the lead 134 includes stimulation electrodes, wherein the stimulation electrodes include a plurality of potential electrode configurations. During an embodiment of a process for implanting the electrodes, the distal end of the lead enters the left subclavian vein 138 through an incision, advances in the subclavian veins and then enters and advances right internal jugular vein 139 until the electrodes reach one or more vagal nerve stimulation sites. The stimulation electrodes are positioned, and repositioned when necessary, using the lead 134 and/or a lead insertion tool such as a stylet, a guide wire, or a guide catheter.

The activity sensor 133 is placed on the neck over the larynx to sense a signal indicative of laryngeal activity. The laryngeal activity is used as a measure of response of vagus nerve 140 to the neural stimulation delivered to the vagus nerve. In various embodiments, the laryngeal activity is monitored for placement of the electrodes and to program stimulation parameters such as those controlling stimulation intensity (e.g., stimulation amplitude, frequency, duration, and duty cycle), and detection or monitoring of various events that affect the response of the vagal nerve to the neural stimulation.

The proximal end of the lead 134 remains outside of the body, such as during an operation of implantation, which allows the electrodes to be placed as desired before connecting the proximal end to an implantable medical device. The proximal end of the lead 134 includes a connector coupled to a connector of cable 137 to allow delivery of the neural stimulation from the external system 135. The external system allows a user such as a physician or other caregiver to control the delivery of neural stimulation and monitor the signal indicative of larynx sensed by activity sensor.

Figure 20:
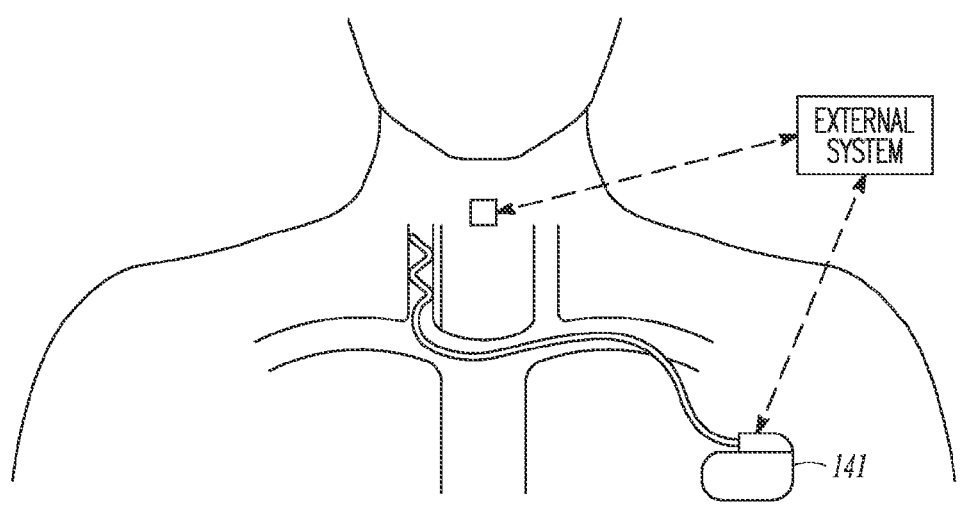

FIG. 20 is an illustration of an embodiment of a neural stimulation system and portions of the environment in which the system is used. The system differs from the system in FIG. 19 primarily in that the neural stimulation is delivered from an implantable medical device 141 implanted in the body. In an embodiment, FIGS. 19 and 20 illustrate different stages of implantation and use of an implantable neural stimulation system, where FIG. 19 illustrates a system setup in the middle of an implantation procedure and FIG. 20 illustrates the system set-up after the implantable neural stimulation system is fully implanted, such as during the end stage of the implantation procedure when the implantable neural stimulation system is programmed for chronic use or during a follow-up examination during which the implantable neural stimulation system is adjusted if necessary. The external system and implantable medical device are communicatively coupled via a telemetry link. In one embodiment, the telemetry link is an inductive telemetry link. In an alternative embodiment, the telemetry link is a far-field radio-frequency telemetry link.

The system embodiments illustrated in FIGS. 19 and 20 include a transvenous lead to stimulate the vagus nerve. As will be understood by those of ordinary skill in the art upon reading and comprehending this disclosure, the present subject matter is not limited to embodiments with transvenous leads nor to embodiments that stimulate the vagus nerve, and the systems illustrated in these figures may be used with leads that are not within blood vessel or with leads that are positioned to stimulate another nerve other than the vagus nerve. Stimulation electrodes may be operationally positioned to lie next to the neural target.

Figure 21:
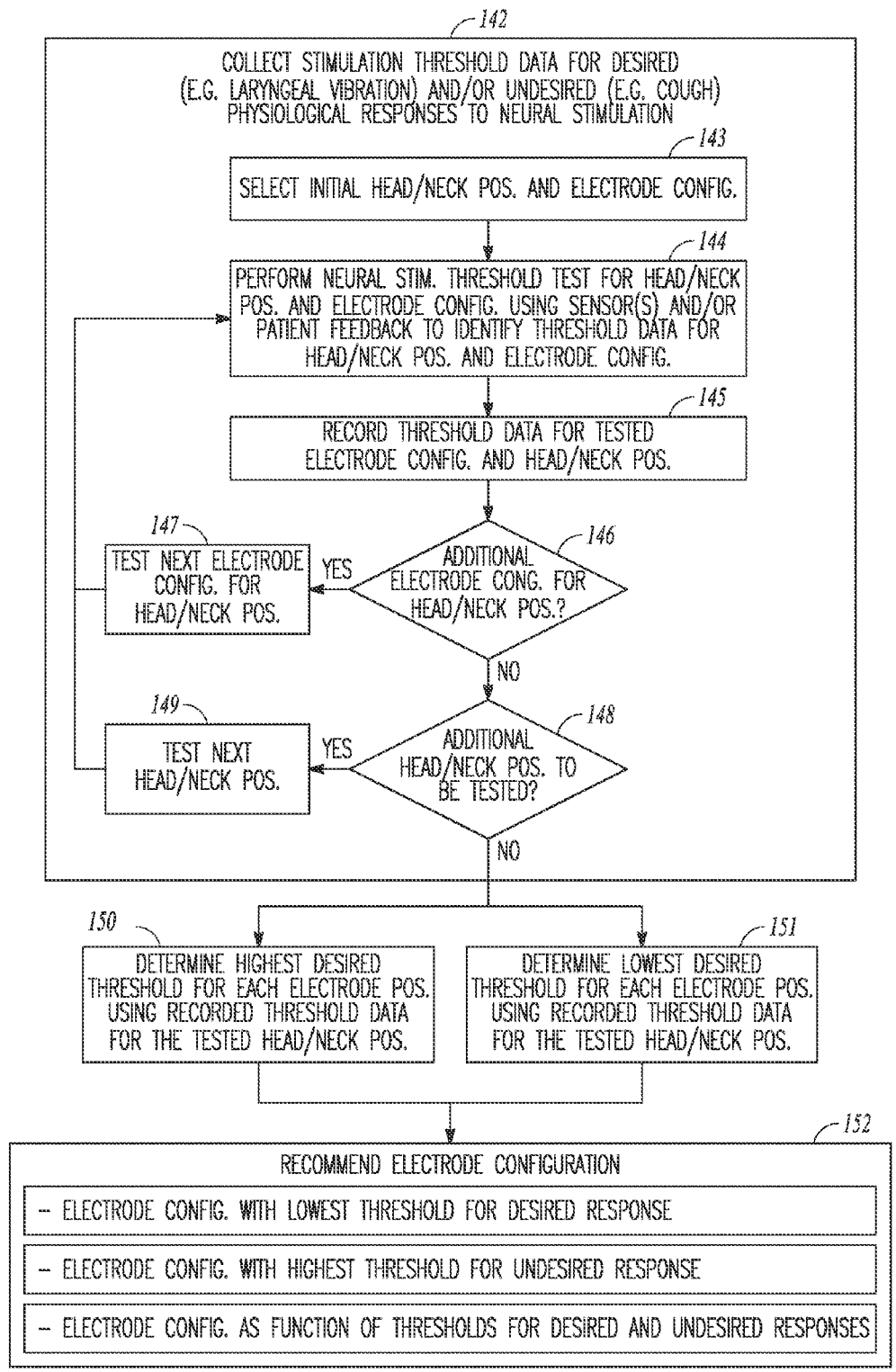
FIG. 21 illustrates an embodiment of a method for recommending an electrode configuration for delivering neural stimulation.

FIG. 21 illustrates an embodiment of a method for recommending an electrode configuration for delivering neural stimulation. The illustrated method generally collects threshold data for desired or undesired responses to the neural stimulation 142. By way of example, desired stimulation threshold values are sensed (e.g. laryngeal vibration) and/or undesired side effect threshold values are sensed (e.g. cough). For an initial head/neck position and electrode configuration 143, a neural stimulation threshold test routine is performed 144. The threshold data may be determined using internal or external sensor(s) and/or using a feedback device through which a person can enter patient feedback information. Patient feedback data may be entered into the pad by the patient or clinician. The threshold test routine delivers neural stimulation and steps through a plurality of stimulation intensity values and through a plurality of electrode configurations for a first head/neck position. At 145, the threshold data for the tested electrode configuration and head/neck position is recorded. The collected thresholds are populated into a table for that head position. If there are additional electrode configurations to be tested for the test head/neck position as determined at 146, then the illustrated method initiates a process at 147 to test the next electrode configuration for the head/neck position. If there are no additional electrode configurations to be tested for the tested head/neck position, then it is determined if there are additional head/neck positions to be tested as determined at 148. The process initiates a test for the next head/neck position if there are additional head/neck positions to be tested. When there are no more head/neck positions to be tested, then the illustrated method proceeds with a process at 149 to make a recommendation based on the measured thresholds.

For each electrode configuration, some system embodiments determine the highest recorded stimulation threshold (e.g. laryngeal capture) for the tested head/neck positions for laryngeal capture, as generally illustrated at 150. For each electrode configuration, some system embodiments determine the lowest side effect threshold (e.g. cough) for the tested head/neck positions, as generally illustrated at 151. Some embodiments look for the desired stimulation threshold and not the side effect stimulation threshold, some embodiments look for the side effect threshold but not the desired stimulation threshold, and some embodiments look for both the desired stimulation threshold and the side effect stimulation threshold. The system makes a recommendation, as generally illustrated at 152, for electrode configuration based on the highest stimulation threshold and/or the lowest side effect threshold. For example, an embodiment prefers electrode configurations that provide the lowest threshold for laryngeal capture. An embodiment prefers the electrode configurations that provide the highest threshold for side effects. Some embodiments provide a recommendation for an electrode configuration that provides both the lowest threshold for laryngeal capture and the highest threshold for side effects. If there are no electrode configurations that satisfy both criteria to provide the lowest threshold for desired response and the highest threshold for the undesired response, then the system determines an appropriate electrode configuration based on a function of thresholds for the desired and undesired response, such as may be appropriate to provide effective therapy that still allows the patient to tolerate the therapy.

Figure 22:
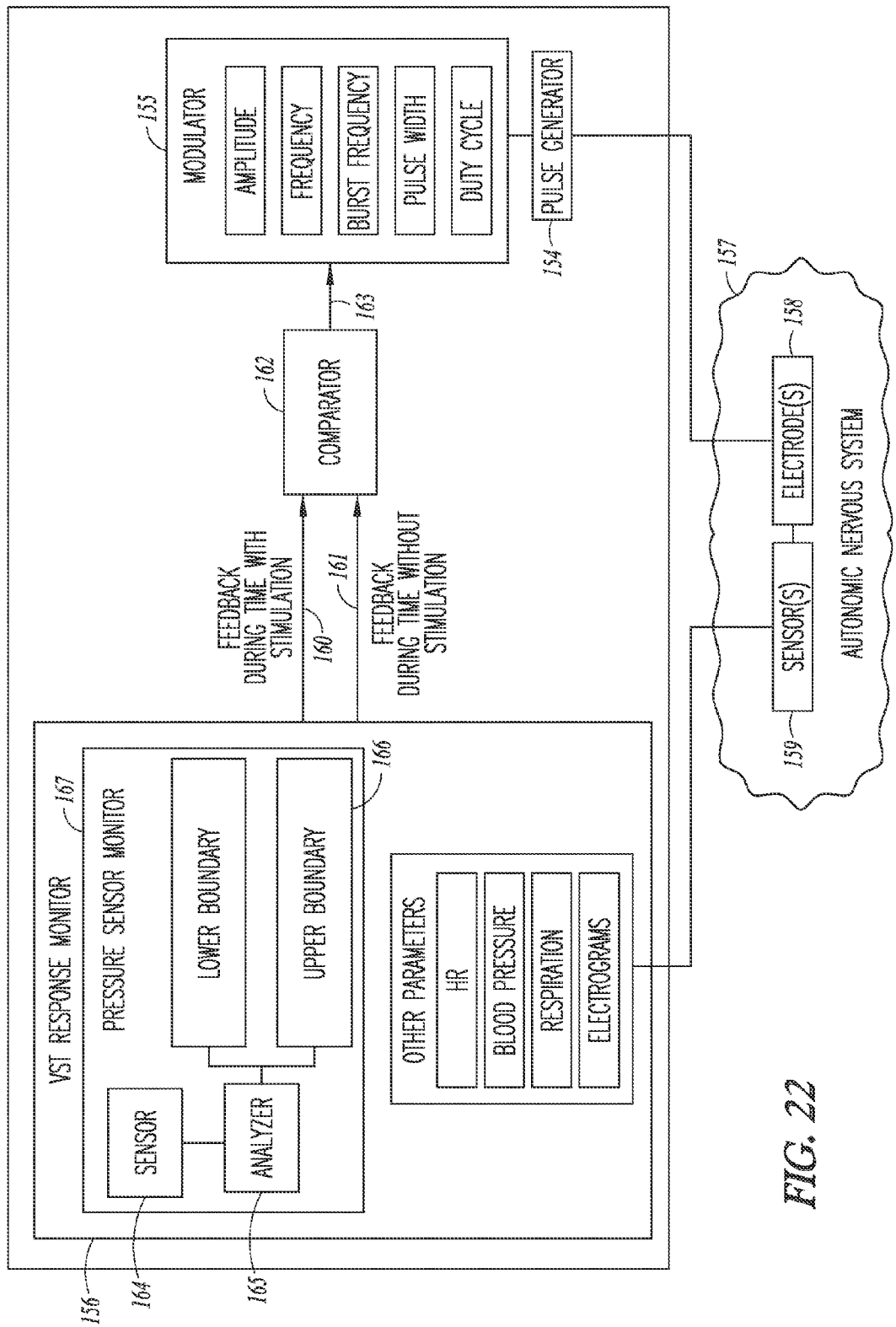
FIG. 22 illustrates a VST system, according to various embodiments.

FIG. 22 illustrates a VST system, according to various embodiments. An implantable device may provide the entire VST system. Some embodiments use external devices to provide the monitoring functions, such as during implantation of an implantable vagus nerve stimulator. Some embodiments use implanted leads and external stimulators. The illustrated VST system 153 includes a pulse generator 154 to provide VST, a modulator 155 to change or modulate intensity of the VST, and a VST response monitor 156 to provide feedback. The autonomic nervous system is generally illustrated at 157. Appropriate electrode(s) 158 are used to provide desired neural stimulation and sensor(s) 159 to sense a parameter that is affected by the neural stimulation. Physiological parameter(s) that quickly respond to VST can be used in closed loop systems or during the implantation process. Examples of such parameters include heart rate, laryngeal vibrations, cough, blood pressure, respiration, and electrogram parameters. Other parameter(s) that have a slower response may be used to confirm that a therapeutically-effective dose is being delivered. The sensor(s) and electrode(s) can be integrated on a single lead or can use multiple leads. Additionally, various system embodiments implement the functions using an implantable neural stimulator capable of communicating with a distinct or integrated implantable cardiac rhythm management device.

The illustrated response monitor 156 monitors the parameter during a time with stimulation to provide a first feedback signal 160 indicative of a parameter value corresponding to a time with stimulation and during a time without stimulation to provide a second feedback signal 161 indicative of a parameter value corresponding to a time without stimulation. The signals 160 and 161 are illustrated as separate lines. These signals 160 and 161 can be sent over different signal paths or over the same signal path. A comparator 162 receives the first and second feedback signals 160 and 161 and determines a detected change in the parameter value based on these signals. Additionally, the comparator compares the detected change with an allowed change, which can be programmed into the device. For example, the device can be programmed to allow a heart rate reduction during VST to be no less than a percentage (e.g. on the order of 95%) of heart rate without stimulation. The device may be programmed with a quantitative value to allow a heart rate reduction during VST to be no less than that quantitative value (e.g. 5 beats per minute) than heart rate without stimulation. A comparison of the detected change (based on signals 160 and 161) and the allowed change provide a comparison result 163, which is used to appropriately control the modulator to adjust the applied VST.

The illustrated device includes a sensor 164 and an analyzer 165 such as, by way of example and not limitation, a variability analyzer or frequency analyzer. The analyzer analyzes a plurality of sensed impedance values to determine if the laryngeal vibrations and/or cough is caused by the neural stimulation. The device is programmed with an upper boundary value 166 such as may represent a cough and a lower boundary 167 such as may represent laryngeal vibrations. The output of the analyzer is compared to the lower and upper boundaries to determine if the VST intensity is out of bounds.

Some embodiments use a therapy protocol that adjusts the VST intensity, limited by the upper boundary for the VST intensity and in some embodiments by the tower boundary for the VST intensity. The VST intensity can be adjusted, within the allowed bounds set by the present subject matter, based on sensed parameters. Some therapy protocols adjust the upper boundary and/or lower boundary for VST intensity based on a schedule (e,g. time of day) or sensed data (e.g. activity).

Various modulator embodiments adjust VST intensity by changing an amplitude of a stimulation signal used to provide VST, by changing a frequency of a stimulation signal used to provide VST, by changing a burst frequency of a stimulation signal used to provide VST, by changing a pulse width of a stimulation signal used to provide VST, by changing a duty cycle of a stimulation signal used to provide VST, or various combinations of two or more of these stimulation signal characteristics.

The illustrated system for delivering VST is useful in extended therapy applications. Examples of extended therapy applications involve applying stimulation to prevent remodeling of cardiac tissue, to reverse remodel cardiac tissue in cardiovascular disease, and to treat hypertension. VST can be applied for a portion (approximately 10 seconds) of each minute, for example. A VST dose may be adjusted by adjusting the duration or duty cycle of the stimulation (e.g. approximately 5 seconds or 15 seconds each minute or approximately 5 to 15 seconds every 30 seconds or approximately 5 to 30 seconds every 2 minutes, or approximately 5 seconds to 3 minutes every 5 minutes or a continuous stimulation). According to an embodiment, the VST non-selectively stimulates both efferent and afferent axons. The illustrated values are provided by way of example, and not limitation. Over the course of days, weeks, months and years, the physiological response to VST can vary for a number of reasons, such as nerve adaptation, tissue encapsulation, fibrosis, impedance changes, and the like. Various closed loop system embodiments monitor at least one parameter that has a quick and predictable response to VST, and uses the monitored parameter to appropriately change the neural stimulation signal to result in a desired stimulation of the parasympathetic nervous system. Some embodiments monitor heart rate. Some embodiments monitor laryngeal vibrations, and adjust VST intensity as necessary for the VST to elicit laryngeal vibrations.

Figure 23:
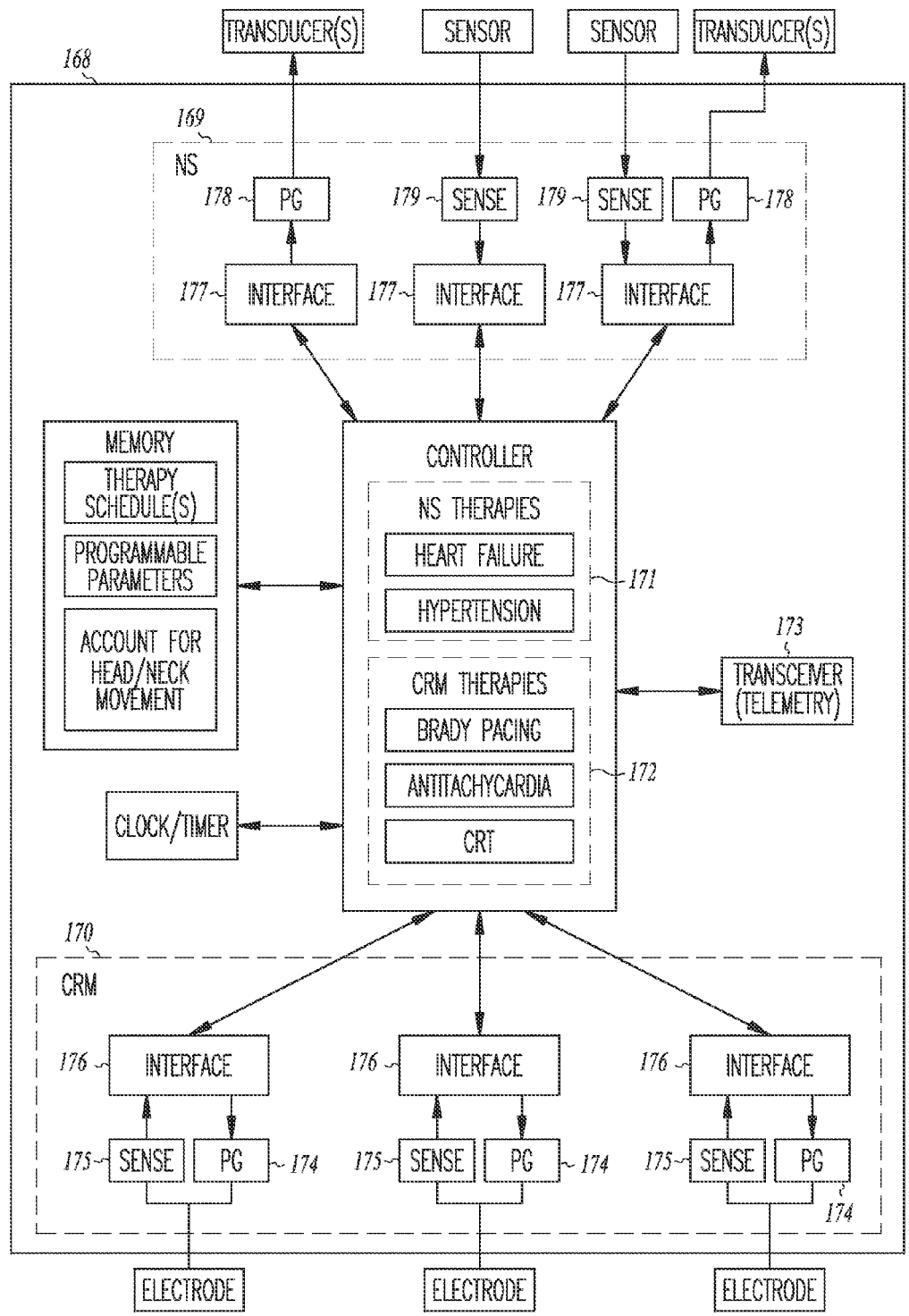
FIG. 23 illustrates an implantable medical device (IMD) having a neural stimulation (NS) component and a cardiac rhythm management (CRM) component according to various embodiments of the present subject matter.

FIG. 23 illustrates an implantable medical device (IMD) 168 having a neural stimulation (NS) component 169 and a cardiac rhythm management (CRM) component 170 according to various embodiments of the present subject matter. The NS and CRM components may reside in the same IMD can. Some embodiments incorporate the NS component and CRM component in separate implantable devices. The coordination of the NS component and CRM component may be managed by a physician or clinician, or may be managed by a programmer or programming within the device(s). The illustrated device includes a controller and memory. According to various embodiments, the controller includes hardware, software, or a combination of hardware and software to perform the neural stimulation and CRM functions. For example, the programmed therapy applications and the algorithms to account for head/neck movement in delivering therapy as discussed in this disclosure are capable of being stored as computer-readable instructions embodied in memory and executed by a processor. For example, therapy schedule(s), programmable parameters and threshold detection or dose setting algorithms such as disclosed herein can be stored in memory. Additionally, some embodiments store a threshold detection routine for detecting a threshold for the neural stimulation, some embodiments store a dose setting routine for titrating the dose, and some embodiments store an algorithm used to make a recommendation for a desired electrode configuration, stimulation vector, and stimulation parameters in which the recommendation accounts for head/neck movement. According to various embodiments, the controller includes a processor to execute instructions embedded in memory to perform the neural stimulation and CRM functions. The illustrated neural stimulation therapy 171 can include VST, such as VST to treat heart failure or other cardiovascular disease. Various embodiments include CRM therapies 172, such as bradycardia pacing, anti-tachycardia therapies such as ATP, defibrillation and cardioversion, and cardiac resynchronization therapy (CRT). The illustrated device further includes a transceiver 173 and associated circuitry for use to communicate with a programmer or another external or internal device. Various embodiments include a telemetry coil.

The CRM therapy component 170 includes components, under the control of the controller, to stimulate a heart and/or sense cardiac signals using one or more electrodes. The illustrated CRM therapy section includes a pulse generator 174 for use to provide an electrical signal through an electrode to stimulate a heart, and further includes sense circuitry 175 to detect and process sensed cardiac signals. An interface 176 is generally illustrated for use to communicate between the controller and the pulse generator and sense circuitry. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy component 169 includes components, under the control of the controller, to stimulate a neural stimulation target and/or sense parameters associated with nerve activity or surrogates of nerve activity such as heart rate, blood pressure, respiration. Three interfaces 177 are illustrated for use to provide neural stimulation. However, the present subject matter is not limited to a particular number of interfaces, or to any particular stimulating or sensing functions. Pulse generators 178 are used to provide electrical pulses to transducer/electrode or transducers/electrodes for use to stimulate a neural stimulation target. According to various embodiments, the pulse generator includes circuitry to set, and in some embodiments change, the amplitude of the stimulation pulse, the pulse width of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 179 are used to detect and process signals from a sensor, such as a sensor of nerve activity, heart rate, blood pressure, respiration, and the like. Sensor(s) may be used to sense laryngeal vibrations. Sensor(s) may be used to detect a state (e.g. accelerometer used to detect activity). The interfaces 177 are generally illustrated for use to communicate between the controller and the pulse generator and sense circuitry. Each interface, for example, may be used to control a separate lead. Various embodiments of the NS therapy section only include a pulse generator to stimulate a neural target. The illustrated device further includes a clock/timer, which can be used to deliver the programmed therapy according to a programmed stimulation protocol and/or schedule.

Figure 24:
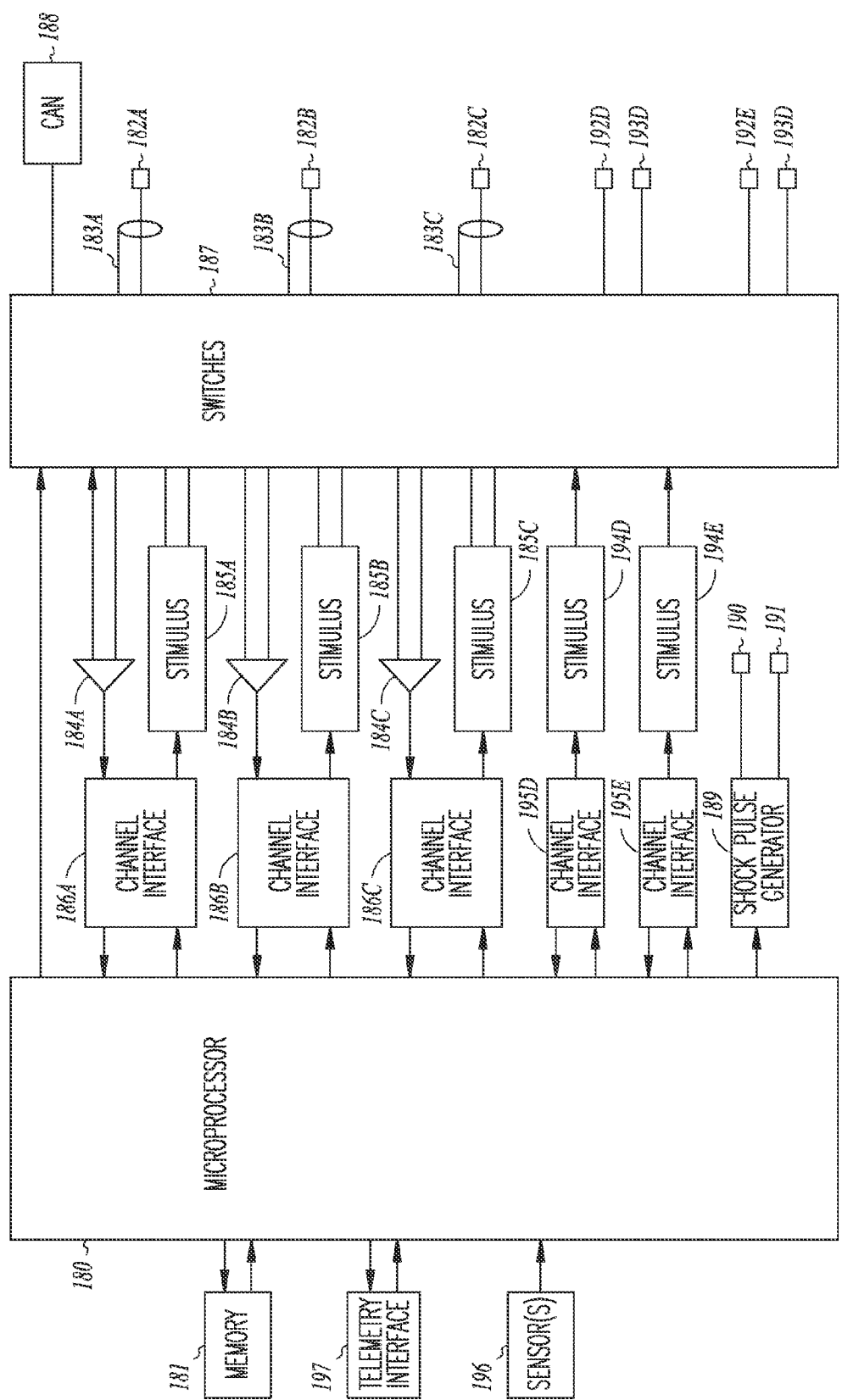
FIG. 24 shows a system diagram of an embodiment of a microprocessor-based implantable device, according to various embodiments.

FIG. 24 shows a system diagram of an embodiment of a microprocessor-based implantable device, according to various embodiments. The controller of the device is a microprocessor 180 which communicates with a memory 181 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 182A-C and tip electrodes 183A-C, sensing amplifiers 184A-C, pacing stimuli 185A-C, and channel interfaces 186A-C. Each channel thus includes a pacing channel made up of the pulse generator connected to the electrode and a sensing channel made up of the sense amplifier connected to the electrode. The channel interfaces 186A-C communicate bidirectionally with the microprocessor 180, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 187 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 188 or an electrode on another lead serving as a ground electrode. A shock pulse generator 189 is also interfaced to the controller for delivering a defibrillation shock via shock electrodes (e.g. electrodes 190 and 191) to the atria or ventricles upon detection of a shockable tachyarrhythmia.

Neural stimulation channels, identified as channels D and E, are incorporated into the device for delivering parasympathetic stimulation and/or sympathetic inhibition, where one channel includes a bipolar lead with a first electrode 192D and a second electrode 193D, a pacing stimulus 194D, and a channel interface 195D, and the other channel includes a bipolar lead with a first electrode 192E and a second electrode 193E, a pacing stimulus 194E, and a channel interface 195E. Other embodiments may use unipolar leads in which case the neural stimulation pulses are referenced to the can or another electrode. Other embodiments may use tripolar or multipolar leads. In various embodiments, the pulse generator for each channel outputs a train of neural stimulation pulses which may be varied by the controller as to amplitude, frequency, and the like. In this embodiment, each of the neural stimulation channels uses a lead which can be intravascularly disposed near an appropriate neural target. Other types of leads and/or electrodes may also be employed. In some embodiments, the leads of the neural stimulation electrodes are replaced by wireless links. Sensor(s) 196 are used by the microprocessor to determine capture (e,g, laryngeal vibrations), the efficacy of therapy (e.g. heart rate, blood pressure) and/or detect events (e.g. cough) or states (e.g. activity sensors).

The figure illustrates a telemetry interface 197 connected to the microprocessor, which can be used to communicate with an external device. The illustrated microprocessor is capable of performing neural stimulation therapy routines and myocardial (CRM) stimulation routines. Examples of NS therapy routines include VST therapies to provide myocardial therapies. NS therapy routines also include routines or algorithms as described in this document. Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT).

Figure 25:
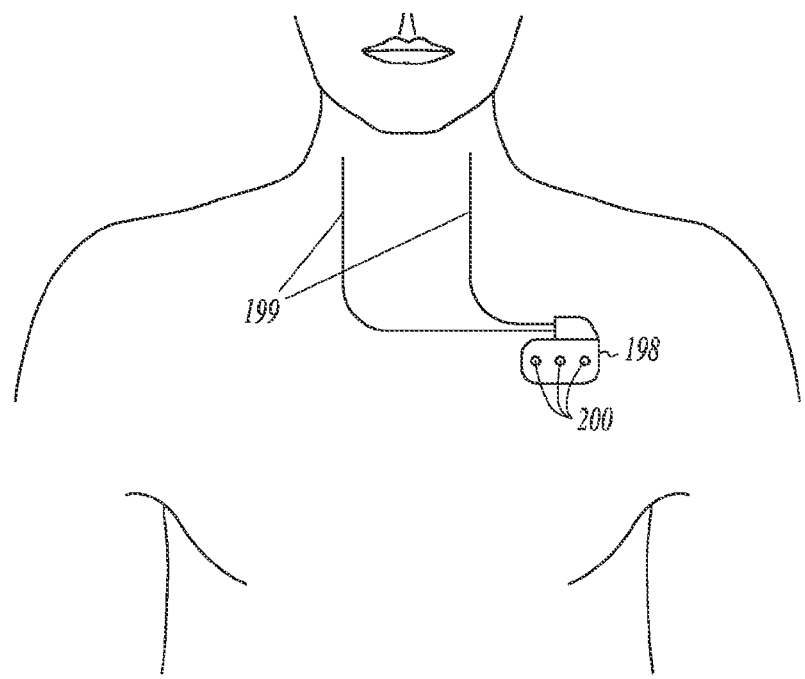
FIGS. 25-26 illustrate system embodiments adapted to provide VST, and are illustrated as bilateral systems that can stimulate both the left and right vagus nerve.
Figure 26:
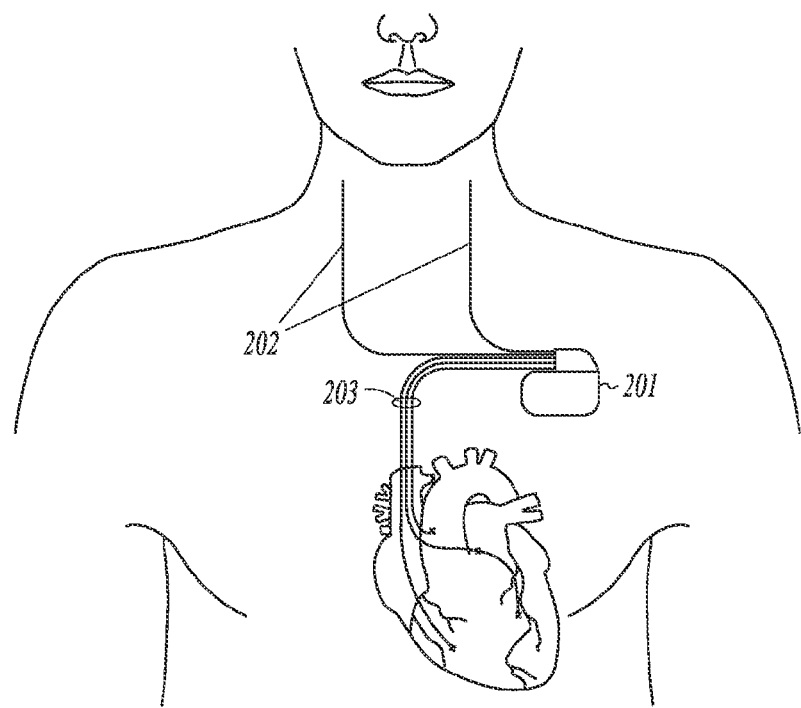

FIGS. 25-26 illustrate system embodiments adapted to provide VST, and are illustrated as bilateral systems that can stimulate both the left and right vagus nerve. Those of ordinary skill in the art will understand, upon reading and comprehending this disclosure, that systems can be designed to stimulate only the right vagus nerve, systems can be designed to stimulate only the left vagus nerve, and systems can be designed to bilaterally stimulate both the right and left vagus nerves. The systems can be designed to stimulate nerve traffic (providing a parasympathetic response when the vagus is stimulated), or to inhibit nerve traffic (providing a sympathetic response when the vagus is inhibited). Various embodiments deliver unidirectional stimulation or selective stimulation of some of the nerve fibers in the nerve. FIGS. 25-26 illustrate the use of a lead to stimulate the vagus nerve. Wireless technology could be substituted for the leads, such that a leadless electrode is adapted to stimulate a vagus nerve and is further adapted to wirelessly communicate with an implantable system for use in controlling the VST.

FIG. 25 illustrates a system embodiment in which an IMD 198 is placed subcutaneously or submuscularly in a patient's chest with lead(s) 199 positioned to stimulate a vagus nerve. According to various embodiments, neural stimulation lead(s) 199 are subcutaneously tunneled to a neural target, and can have a nerve cuff electrode to stimulate the neural target. Some vagus nerve stimulation lead embodiments are intravascularly fed into a vessel proximate to the neural target, and use electrode(s) within the vessel to transvascularly stimulate the neural target. For example, some embodiments stimulate the vagus using electrode(s) positioned within the internal jugular vein. Other embodiments deliver neural stimulation to the neural target from within the trachea, the laryngeal branches of the internal jugular vein, and the subclavian vein. The neural targets can be stimulated using other energy waveforms, such as ultrasound and light energy waveforms. The illustrated system includes leadless ECG electrodes 200 on the housing of the device. These ECG electrodes are capable of being used to detect heart rate, for example.

FIG. 26 illustrates an IMD 201 placed subcutaneously or submuscularly in a patient's chest with lead(s) 202 positioned to provide a CRM therapy to a heart, and with lead(s) 203 positioned to stimulate and/or inhibit neural traffic at a neural target, such as a vagus nerve, according to various embodiments. According to various embodiments, neural stimulation lead(s) are subcutaneously tunneled to a neural target, and can have a nerve cuff electrode to stimulate the neural target. Some lead embodiments are intravascularly fed into a vessel proximate to the neural target, and use transducer(s) within the vessel to transvascularly stimulate the neural target. For example, some embodiments target the vagus nerve using electrode(s) positioned within the internal jugular vein.

Figure 27:
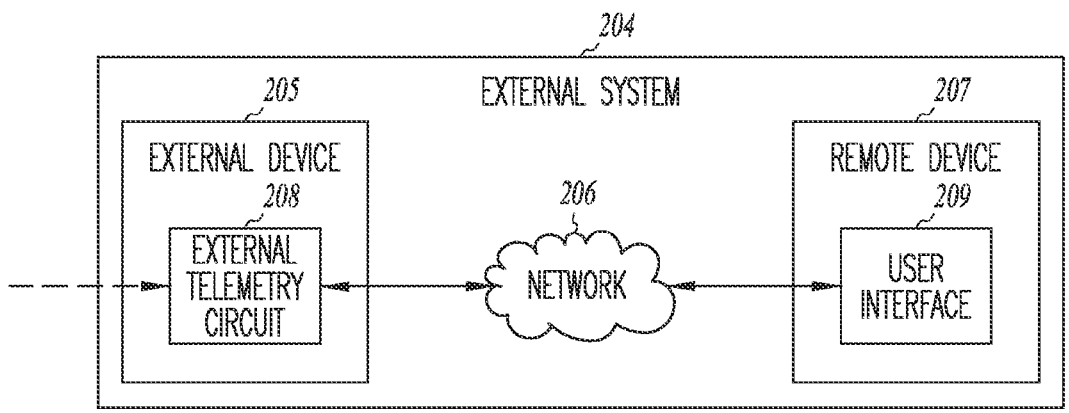
FIG. 27 is a block diagram illustrating an embodiment of an external system.

FIG. 27 is a block diagram illustrating an embodiment of an external system 204. The external system includes a programmer, in some embodiments. In the illustrated embodiment, the external system includes a patient management system. As illustrated, the external system is a patient management system including an external device 205, a telecommunication network 206, and a remote device 207. The external device 205 is placed within the vicinity of an implantable medical device (IMD) and includes an external telemetry system 208 to communicate with the IMD. The remote device(s) is in one or more remote locations and communicates with the external device through the network, thus allowing a physician or other caregiver to monitor and treat a patient from a distant location and/or allowing access to various treatment resources from the one or more remote locations. The illustrated remote device includes a user interface 209. According to various embodiments, the external device includes a neural stimulator, a programmer or other device such as a computer, a personal data assistant or phone. The external device, in various embodiments, includes two devices adapted to communicate with each other over an appropriate communication channel, such as a computer by way of example and not limitation. The external device can be used by the patient or physician to provide feedback indicative of patient discomfort, for example.

As will be understood by one of ordinary skill in the art upon reading and comprehending the present subject matter, various embodiments of the present subject matter improve the ability to quickly and accurately implant and program a neural stimulation system and intermittently reprogram the system, improve patient acceptance of therapy and maintain efficacious levels of therapy. The modules and other circuitry shown and described herein can be implemented using software, hardware, firmware and combinations thereof.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method, comprising:
   performing a neural stimulation test routine for stimulating a neural target in a cervical region of a patient, wherein a patient's head is moved into a plurality of positions including a plurality of selected head positions for threshold testing, and for each of a plurality of selected head positions, performing the neural stimulation test routine includes using a neural stimulator and electrodes to deliver neural stimulation to test a plurality of electrode configurations to provide threshold data, and collecting the threshold data;
   recording the threshold data for each of the tested electrode configurations for the plurality of selected head positions; and
   recommending an electrode configuration based on the recorded threshold data using an algorithm executed by a processor.

2. The method of claim 1, wherein performing the neural stimulation test routine includes using at least one intravascular electrode to transvascularly deliver neural stimulation to the neural target.

3. The method of claim 1, wherein performing the neural stimulation test routine includes using at least one electrode in a carotid sheath of the patient to stimulate the neural target.

4. The method of claim 1, wherein performing the neural stimulation test routine includes using at least one electrode lying next to the neural target.

5. The method of claim 1, wherein testing the plurality of electrode configurations includes testing a desired response threshold, the desired response threshold representing a threshold for obtaining a desired physiological response to neural stimulation.

6. The method of claim 5, wherein the neural target is a cervical vagus nerve and the desired response threshold is a laryngeal vibration threshold.

7. The method of claim 5, further comprising
   determining a highest desired response threshold for each of the electrode configurations using recorded threshold data for each of the selected head positions,
   wherein recommending the electrode configuration based on the recorded threshold data includes recommending an electrode configuration having a lowest value for the highest desired response thresholds.

8. The method of claim 7, wherein the threshold data includes a threshold current amplitude, the method further comprising recommending a stimulation current for the recommended electrode configuration, wherein the recommended stimulation current has an amplitude corresponding to the threshold current amplitude with a safety factor.

9. The method of claim 1, wherein testing the threshold for the plurality of tested electrode configurations includes testing an undesired response threshold, the undesired response threshold representing a threshold for obtaining an undesired physiological response to neural stimulation.

10. The method of claim 9, wherein the neural target is a cervical vagus nerve and wherein testing an undesired response threshold to neural stimulation includes receiving patient-entered or clinician-entered feedback to provide the threshold data.

11. The method of claim 9, wherein the neural target is a cervical vagus nerve and the undesired resp onse threshold is a cough threshold.

12. The method of claim 9, further comprising determining a lowest undesired threshold for each electrode configuration using recorded threshold data for each head position, wherein recommending the electrode configuration based on the recorded threshold data includes recommending an electrode configuration having a highest value for the lowest undesired response thresholds.

13. The method of claim 1, wherein testing the threshold for the plurality of tested electrode configurations includes testing both a desired response threshold and an undesired response threshold, the desired response threshold representing a threshold for obtaining a desired physiological response to the neural stimulation and the undesired response threshold representing a threshold for obtaining an undesired physiological response to the neural stimulation.

14. The method of claim 13, further comprising:
   determining both a highest desired response threshold and a lowest undesired response threshold for each electrode configuration using recorded threshold data for each of the head positions;
   determining a lowest value for the highest desired response thresholds; and
   determining a highest value for the lowest undesired thresholds,
   wherein recommending the electrode configuration includes recommending the electrode configuration as a function of both the lowest value for the highest desired resp onse thresholds and the highest value for the lowest undesired response thresholds.

15. The method of claim 14, wherein the threshold data is sensed using a pressure sensor, an accelerometer, a minute ventilation sensor, an impedance sensor, a sensor configured to detect an electrocardiogram (EKG), a sensor configured to detect an electromyogram (EMG), or a blood pressure sensor.

16. The method of claim 1, wherein testing the threshold for the plurality of tested electrode configurations includes receiving p atient-entered or clinician-entered feedback to provide the threshold data.

17. The method of claim 1, wherein testing the threshold for the plurality of tested electrode configurations includes using an implanted sensor or an external sensor to sense the threshold data.

18. A method, comprising:
- performing a neural stimulation test routine for stimulating a neural target in a cervical region of a patient, wherein a patient's head is moved into a plurality of positions including a plurality of selected head positions for threshold testing.and for each of a plurality of selected head positions, performing the neural stimulation test routine includes using a neural stimulator to deliver neural stimulation to test a plurality of electrode configurations to provide threshold data for a desired response threshold and collecting the threshold data, the desired response threshold representing a threshold for obtaining a desired physiological response to the neural stimulation;
- recording the threshold data for each of the tested electrode configurations for the plurality of selected head positions; and
- recommending an electrode configuration based on the recorded threshold data using an algorithm executed by a processor.

19. The method of claim 18, wherein testing the threshold for the plurality of tested electrode configurations includes testing an undesired response threshold, the undesired response threshold representing a threshold for obtaining an undesired physiological response to the neural stimulation.

20. The method of claim 18, wherein testing the threshold for the plurality of tested electrode configurations includes receiving patient-entered or clinician-entered feedback to provide the threshold data.

21. The method of claim 18, wherein testing the threshold for the plurality of tested electrode configurations includes using an implanted sensor or an external sensor to sense the threshold data.

22. The method of claim 21, wherein the threshold data is sensed using a pressure sensor, an accelerometer, a minute ventilation sensor, an impedance sensor, a sensor configured to detect an electrocardiogram (EKG), a sensor configured to detect an electromyogram (EM G), or a blood pressure sensor.

23. The method of claim 18, wherein the neural target is a cervical vagus nerve and the desired response threshold is a laryngeal vibration threshold.

24. The method of claim 23, further comprising:
- determining a highest desired response threshold for each of the electrode configurations using recorded threshold data for each of the selected head positions,
- wherein recommending the electrode configuration based on the recorded threshold data includes recommending an electrode configuration having a lowest value for the highest desired response thresholds.

25. The method of claim 24, wherein the threshold data includes a threshold current amplitude, the method further comprising recommending a stimulation current for the recommended electrode configuration, wherein the recommended stimulation current has an amplitude corresponding to the threshold current amplitude with a safety factor.

* * * * *